(12) United States Patent
Moore et al.

(10) Patent No.: US 12,728,268 B2
(45) Date of Patent: Sep. 8, 2026

(54) CLOUD BASED NEUROSTIMULATION PROGRAMMING OPTIMIZATION

(71) Applicant: Boston Scientific Neuromodulation Corporation, Valencia, CA (US)

(72) Inventors: Lisa Denise Moore, Glendale, CA (US); Hemant Bokil, Cambridge, MA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 307 days.

(21) Appl. No.: 18/581,255

(22) Filed: Feb. 19, 2024

(65) Prior Publication Data

US 2024/0285952 A1 Aug. 29, 2024

Related U.S. Application Data

(60) Provisional application No. 63/448,065, filed on Feb. 24, 2023.

(51) Int. Cl.
*A61N 1/36* (2006.01)
*A61N 1/05* (2006.01)

(52) U.S. Cl.
CPC ..... *A61N 1/36139* (2013.01); *A61N 1/36067* (2013.01); *A61N 1/36132* (2013.01);
(Continued)

(58) Field of Classification Search
CPC ............ A61N 1/36139; A61N 1/36067; A61N 1/36132; A61N 1/36153; A61N 1/36157; A61N 1/36185; A61N 1/0534
See application file for complete search history.

(56) References Cited

U.S. PATENT DOCUMENTS 10,357,657 B2 7/2019 Moffitt et al.
10,603,498 B2 3/2020 Blum et al.
(Continued)

FOREIGN PATENT DOCUMENTS

WO 2024177933 8/2024

OTHER PUBLICATIONS

"International Application Serial No. PCT US2024 016376, International Search Report mailed Jun. 20, 2024", 3 pgs.
(Continued)

*Primary Examiner* — Paula J Stice
(74) *Attorney, Agent, or Firm* — Schwegman Lundberg & Woessner, P.A.

(57) ABSTRACT

Systems and methods for optimizing electrostimulation in a patient is discussed. An exemplary system includes an implantable stimulator to provide electrostimulation, a programming device for in-clinic stimulation testing, an a therapy titration device for in-home therapy titration. In response to electrostimulation delivered in accordance with first stimulation settings defined in an electrode configuration and parameter value search space, the programing device evaluates patient clinical response in the patient, and determines a subspace of the search space based on the clinical response. During an in-home therapy titration phase, the therapy titration device can use cloud-based services to evaluate clinical responses to electrostimulation in accordance with candidate stimulation settings defined in the identified subspace. Based on the clinical response indicator, the therapy titration device can select from the candidate stimulation settings an optimal stimulation setting for future electrostimulation therapy in the patient.

20 Claims, 10 Drawing Sheets

(52) U.S. Cl.
CPC ..... *A61N 1/36153* (2013.01); *A61N 1/36157* (2013.01); *A61N 1/36185* (2013.01); *A61N 1/0534* (2013.01)

(56) References Cited

U.S. PATENT DOCUMENTS

| | | | |
|---|---|---|---|
| 2018/0104500 A1 | 4/2018 | Blum et al. | |
| 2020/0001091 A1 | 1/2020 | Marnfeldt | |
| 2020/0368532 A1 | 11/2020 | King et al. | |
| 2020/0398057 A1 | 12/2020 | Esteller et al. | |
| 2021/0052901 A1* | 2/2021 | Pepin ................ | A61N 1/37282 |
| 2021/0196956 A1 | 7/2021 | Juárez Paz | |
| 2021/0339024 A1 | 11/2021 | Naor et al. | |
| 2022/0184401 A1* | 6/2022 | Vaidyanathan .... | A61N 1/36139 |
| 2022/0266032 A1* | 8/2022 | Molina .............. | A61N 1/37247 |
| 2022/0355114 A1 | 11/2022 | Moore et al. | |
| 2022/0355115 A1 | 11/2022 | Moore et al. | |
| 2022/0379127 A1 | 12/2022 | Huertas Fernandez et al. | |
| 2023/0271015 A1 | 8/2023 | Malekmohammadi et al. | |
| 2024/0065620 A1 | 2/2024 | Moore et al. | |
| 2024/0198110 A1 | 6/2024 | Moore | |

OTHER PUBLICATIONS

"International Application Serial No. PCT US2024 016376, Written Opinion mailed Jun. 20, 2024", 5 pgs.
"International Application Serial No. PCT US2024 016376, International Preliminary Report on Patentability mailed Sep. 4, 2025", 7 pgs.

* cited by examiner

In-Clinic Phase

In-home Phase

FIG. 9

CLOUD BASED NEUROSTIMULATION PROGRAMMING OPTIMIZATION

CLAIM OF PRIORITY

This application claims the benefit of U.S. Provisional Application No. 63/448,065 filed on Feb. 24, 2023, which is hereby incorporated by reference in its entirety.

TECHNICAL FIELD

This document relates generally to medical devices, and more particularly, to systems, devices and methods for programming a stimulation system to provide neurostimulation to a patient.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS systems have been used as a therapeutic modality for the treatment of chronic pain syndromes and are of increasing interest to treat other conditions including autonomic dysfunction. PNS has been used to treat chronic pain syndrome and incontinence, with a number of other applications under investigation. FES systems have been applied to restore some functionality to paralyzed extremities in spinal cord injury patients. DBS can be used to treat a variety of diseases or disorders.

Stimulation systems, such as implantable electrostimulators, have been developed to provide therapy for a variety of treatments. An implantable electrostimulator can include a pulse generator and one or more leads each including a plurality of stimulation electrodes. The stimulation electrodes are in contact with or near target tissue to be modulated, such as nerves, muscles, or other tissue. The control module generates a control signal to the pulse generator, which generates electrostimulation pulses that are delivered by the electrodes to the target tissue in accordance with an electrode configuration and a set of stimulation parameters.

SUMMARY

Various examples discussed in this document may provide more effective control of neuromodulation therapy such as deep brain stimulation (DBS) in a patient. In accordance with some embodiments, a search space of electrode configurations and parameter values, or a subspace thereof, can be determined during an in-clinic testing and programming session. In subsequent one or more in-home therapy titration sessions, a user (e.g., the patient or an authorized personnel such as a caregiver of the patient) may use a remotely controlled device to determine an optimal stimulation setting from the search space or the subspace. Cloud-based algorithms may be used to guide the in-home therapy optimization within the search space or subspace. As therapy optimization for a patient can be a time-consuming process, by distributing the therapy optimization between the in-clinic testing and programming session and one or more in-home therapy titration sessions, clinician's time and effort spent for in-clinic testing and programming can be reduced. The in-home therapy titration allows the patient to customize the stimulation setting to better address individual needs under evolving medical conditions. In some examples, the in-home therapy titration may be performed in multiple sessions extended over a period of days or weeks. This may help address stimulation wash in effect while giving more timely, real-world patient feedback including a higher volume and a wide variety of clinical response variables, such as motor symptoms or non-motor symptoms that are significant to the patient.

The description that follows will generally focus on the use of the invention within a DBS system, such as that disclosed in U.S. Patent Application Publication 2020/0001091, which is incorporated herein by reference. However, the present invention may find applicability with any implantable neurostimulator device system, including Spinal Cord Stimulation (SCS) systems, Vagus Nerve Stimulation (VNS) system, Sacral Nerve Stimulation (SNS) systems, and the like. The following examples illustrate various aspects of the examples described herein.

Example 1 is a system for providing electrostimulation to a patient. The system comprises an implantable stimulator configured to provide electrostimulation to a neural target of the patient via a lead comprising a plurality of electrodes; and a programming device configured to: under a first patient state, evaluate a clinical response indicator using clinical effect data collected from the patient in response to electrostimulation delivered in accordance with first stimulation settings defined in a search space of electrode configurations and parameter values for the lead with respect to the neural target; and identify a subspace of the search space based at least in part on the clinical response indicator associated with the first stimulation settings; and a therapy titration device configured to: under a second patient state different from the first patient state, evaluate the clinical response indicator using clinical effect data collected from the patient in response to electrostimulation delivered in accordance with candidate stimulation settings defined in the identified subspace; select a stimulation setting from the candidate stimulation settings based at least in part on the clinical response indicator associated with the candidate stimulation settings; and generate a control signal to the implantable stimulator to deliver electrostimulation in accordance with the selected stimulation setting.

In Example 2, the subject matter of Example 1 optionally includes the programming device that can be configured to: without delivering electrostimulation to the patient, estimate clinical effect data for second stimulation settings defined in the search space different than the first stimulation settings based at least on the collected clinical effect data corresponding to the first stimulation settings; evaluate the clinical response indicator further using the estimated clinical effect data; and identify the subspace further based on the clinical response indicator associated with the second stimulation settings.

In Example 3, the subject matter of Example 2 optionally includes the programming device that can be configured to estimate the clinical effect data for the second stimulation settings using a trained machine-learning model.

In Example 4, the subject matter of any one or more of Examples 2-3 optionally includes the programming device that can be further configured to: determine, under the first patient state, at least one base stimulation setting corresponding to the clinical response indicator associated with the first stimulation settings or the second stimulation settings satisfying a specific condition, the at least one base stimulation setting including an optimal electrode configuration and an optimal stimulation parameter value; and identify the subspace based on the clinical response indicator of the at least one base stimulation setting.

In Example 5, the subject matter of any one or more of Examples 1-4 optionally includes the identified subspace that comprises stimulation positions and a stimulation parameter value zone defined between first and second characteristic parameter values for each of the stimulation positions, the first and second characteristic parameter values each corresponding to respective clinical response indicators satisfying respective conditions, wherein the selected stimulation setting has a stimulation parameter value falling within the stimulation parameter value zone.

In Example 6, the subject matter of Example 5 optionally includes the stimulation parameter value zone that can be defined between the first and second characteristic parameter values each modified by respective margins.

In Example 7, the subject matter of any one or more of Examples 5-6 optionally includes the stimulation parameter that can include a stimulation amplitude, the stimulation parameter value zone includes a stimulation amplitude zone defined between (i) a first characteristic stimulation amplitude corresponding to a clinical response indicator indicating an improvement in patient symptom from a baseline and (ii) a second stimulation amplitude corresponding to a clinical response indicator indicating a side effect or a loss of improvement of patient symptom from the baseline.

In Example 8, the subject matter of any one or more of Examples 5-7 optionally includes the stimulation positions that can include a plurality of vertical electrode locations on the lead, and wherein the stimulation parameter value zone comprises stimulation parameter value ranges for the plurality of vertical electrode locations.

In Example 9, the subject matter of any one or more of Examples 5-8 optionally includes the stimulation positions that can include a plurality of directional electrode locations at a common vertical location on the lead, and wherein the stimulation parameter value zone comprises stimulation parameter value ranges for the plurality of directional electrode locations.

In Example 10, the subject matter of any one or more of Examples 1-9 optionally includes the therapy titration device that can be configured to be communicatively coupled to a cloud-computing system, and to use cloud-based services from the cloud-computing system to evaluate the clinical response indicator or to select the stimulation setting.

In Example 11, the subject matter of Example 10 optionally includes the cloud-based services that can include automatically downloading one or more the candidate stimulation settings into the therapy titration device and initiating the electrostimulation in accordance with the candidate stimulation settings.

In Example 12, the subject matter of Example 11 optionally includes the therapy titration device that can include a user interface configured to receive a user input to intervene the electrostimulation delivered in accordance with candidate stimulation settings, or to confirm or modify the selected stimulation setting.

In Example 13, the subject matter of any one or more of Examples 10-12 optionally includes the cloud-based services that can include collecting and storing in a cloud storage the clinical effect data in response to the electrostimulation delivered in accordance with candidate stimulation settings.

In Example 14, the subject matter of Example 13 optionally includes the therapy titration device that can be configured to collect the clinical effect data including at least one of: a user feedback on clinical effects of the electrostimulation via a user interface; or sensor signals sensed by one or more sensors in response to the electrostimulation delivered in accordance with candidate stimulation settings.

In Example 15, the subject matter of any one or more of Examples 1-14 optionally includes the implantable stimulator that can be configured to provide deep brain electrostimulation (DBS) to a brain target via one or more leads each configured to be positioned in a left or right hemisphere of the brain; the programming device that can be configured to identify a first subspace comprising stimulation positions and the stimulation parameter values or value ranges for DBS of the left hemisphere of the brain, and to separately identify a second subspace comprising stimulation positions and the stimulation parameter values or value ranges for DBS of the right hemisphere of the brain; and the therapy titration device is configured to select a first stimulation setting from the first subspace for the DBS of the left hemisphere, and a second stimulation setting from the second subspace for the DBS of the right hemisphere.

Example 16 is a method of providing electrostimulation using a medical-device system, the method comprising: under a first patient state, delivering electrostimulation to a neural target using an implantable stimulator coupled to a lead comprising a plurality of electrodes, the electrostimulation delivered in accordance with first stimulation settings defined in a search space of electrode configurations and parameter values; collecting clinical effect data from the patient in response to the electrostimulation and evaluating a clinical response indicator using the collected clinical effect data; identifying a subspace of the search space based at least in part on the clinical response indicator associated with the first stimulation settings; under a second patient state different from the first patient state, delivering electrostimulation to the neural target using the implantable stimulator, the electrostimulation delivered in accordance with candidate stimulation settings defined in the identified subspace; collecting clinical effect data from the patient in response to the electrostimulation and evaluating a clinical response indicator using the collected clinical effect data; selecting a stimulation setting from the candidate stimulation settings based at least in part on the clinical response indicator associated with the candidate stimulation settings; and generating a control signal to the implantable stimulator to deliver electrostimulation in accordance with the selected stimulation setting.

In Example 17, the subject matter of Example 16 optionally includes: without delivering electrostimulation to the patient, estimating clinical effect data for second stimulation settings defined in the search space different than the first stimulation settings based at least on the collected clinical effect data corresponding to the first stimulation settings; evaluating the clinical response indicator further using the estimated clinical effect data; and identifying the subspace further based on the clinical response indicator associated with the second stimulation setting.

In Example 18, the subject matter of any one or more of Examples 16-17 optionally include, wherein the identified subspace comprises stimulation positions and a stimulation parameter value zone defined between first and second characteristic parameter values for each of the stimulation positions, the first and second characteristic parameter values each corresponding to respective clinical response indicators satisfying respective conditions, wherein the selected stimulation setting has a stimulation parameter value falling within the stimulation parameter value zone.

In Example 19, the subject matter of Example 18 optionally includes the stimulation parameter value zone that can be defined between the first and second characteristic parameter values each modified by respective margins.

In Example 20, the subject matter of any one or more of Examples 18-19 optionally includes the stimulation parameter that can include a stimulation amplitude, the stimulation parameter value zone includes a stimulation amplitude zone defined between (i) a first characteristic stimulation amplitude corresponding to a clinical response indicator indicating an improvement in patient symptom from a baseline and (ii) a second stimulation amplitude corresponding to a clinical response indicator indicating a side effect or a loss of improvement of patient symptom from the baseline.

In Example 21, the subject matter of any one or more of Examples 16-20 optionally includes: receiving cloud-based services from a cloud-computing system; and using the received cloud-based services to initiate the electrostimulation in accordance with the candidate stimulation settings, to evaluate the clinical response indicator, or to select the stimulation setting.

In Example 22, the subject matter of Example 21 optionally includes the cloud-based services that can include collecting and storing in a cloud storage the clinical effect data in response to the electrostimulation delivered in accordance with candidate stimulation settings, wherein the clinical effect data includes at least one of a user feedback on clinical effects of the electrostimulation via a user interface, or sensor signals sensed by one or more sensors in response to the electrostimulation delivered in accordance with candidate stimulation settings.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various examples are illustrated by way of example in the figures of the accompanying drawings. Such examples are demonstrative and not intended to be exhaustive or exclusive examples of the present subject matter.

FIG. 9 illustrates a diagram of an electrode configuration and parameter search space, a subspace thereof, and a 2D monopolar review of characteristic stimulation amplitudes corresponding to directional mode stimulation.

DETAILED DESCRIPTION

This document describes systems and methods for creating, maintaining, and remotely modifying stimulation settings for a neuromodulation therapy such as deep brain stimulation (DBS). According to one embodiment, an exemplary electrostimulation system comprises an implantable stimulator, a programming device to program neurostimulation, and a therapy titration device. The programming device can evaluate, such as in a clinical setting, a clinical response indictor using clinical effect data collected from the patient in response to electrostimulation delivered in accordance with first stimulation settings defined in a search space of electrode configurations and parameter values with respect to the neural target. Based on the clinical response indicator associated with the first stimulation settings, the programming device can identify a subspace of the search space. The subspace comprises a subset of electrode locations and stimulation parameter values or value ranges at the subset of the electrode locations. In subsequent on or more in-home therapy titration sessions, the therapy titration device can evaluate the clinical response indicator using clinical effect data collected from the patient in response to electrostimulation delivered in accordance with candidate stimulation settings that are defined within the identified subspace, and select a stimulation setting from the candidate stimulation settings based on the clinical response indicator. The implantable stimulator can deliver electrostimulation in accordance with the selected stimulation setting.

Various examples described herein involve deep brain stimulation (DBS). The following detailed description of the present subject matter refers to the accompanying drawings which show, by way of illustration, specific aspects and examples in which the present subject matter may be practiced. These examples are described in sufficient detail to enable those skilled in the art to practice the present subject matter. Other examples may be utilized and structural, logical, and electrical changes may be made without departing from the scope of the present subject matter. References to "an", "one", or "various" examples in this disclosure are not necessarily to the same example, and such references contemplate more than one example. The following detailed description is, therefore, not to be taken in a limiting sense, and the scope is defined only by the appended claims, along with the full scope of legal equivalents to which such claims are entitled.

Figure 1:
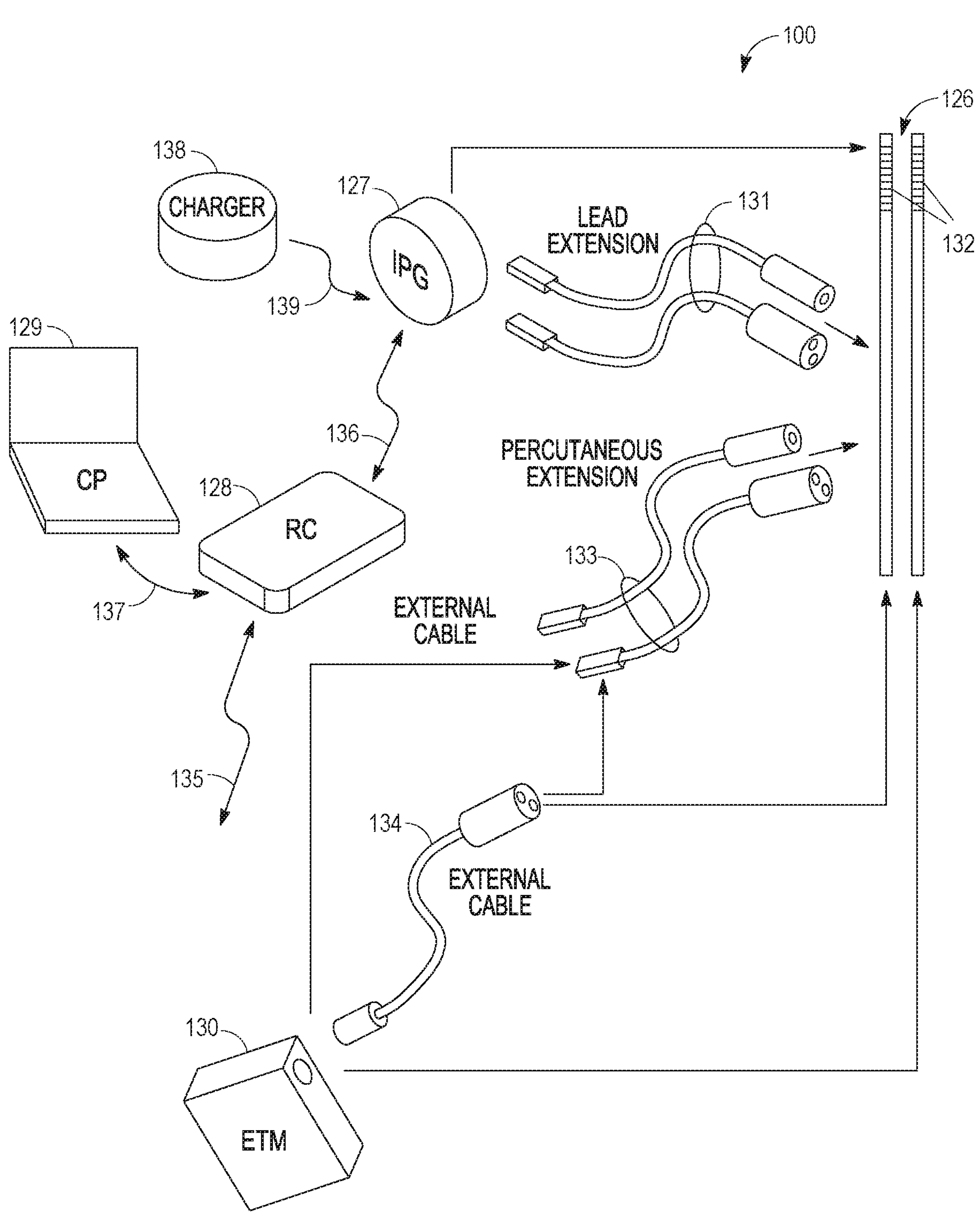
FIG. 1 illustrates an example of an electrical stimulation system that may be used to deliver deep brain stimulation (DBS).

FIG. 1 illustrates, by way of example, an example of an electrical stimulation system 100, which may be used to deliver DBS. The electrical stimulation system 100 may generally include a one or more (illustrated as two) of implantable neuromodulation leads 126, an implantable pulse generator (IPG) 127, an external remote controller (RC) 128, a clinician programmer (CP) 129, and an external trial modulator (ETM) 130. The IPG 127 may be physically connected via one or more percutaneous lead extensions 131 to the neuromodulation lead(s) 126, which carry a plurality of electrodes 132. The electrodes, when implanted in a patient, form an electrode arrangement. As illustrated, the neuromodulation leads 126 may be percutaneous leads with the electrodes arranged in-line along the neuromodulation leads or about a circumference of the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 127 includes pulse generation circuitry that delivers electrical modulation energy in the form of a pulsed electrical waveform (i.e., a temporal series of electrical pulses) to the electrodes in accordance with a set of modulation parameters.

The ETM 130 may also be physically connected via the percutaneous lead extensions 133 and external cable 134 to the neuromodulation lead(s) 126. The ETM 130 may have similar pulse generation circuitry as the IPG 127 to deliver electrical modulation energy to the electrodes in accordance with a set of modulation parameters. The ETM 130 is a non-implantable device that may be used on a trial basis after the neuromodulation leads 126 have been implanted and prior to implantation of the IPG 127, to test the responsiveness of the modulation that is to be provided. Functions described herein with respect to the IPG 127 can likewise be performed with respect to the ETM 130.

The RC 128 may be used to telemetrically control the ETM 130 via a bi-directional RF communications link 135. The RC 128 may be used to telemetrically control the IPG 127 via a bi-directional RF communications link 136. Such control allows the IPG 127 to be turned on or off and to be programmed with different modulation parameter sets. The IPG 127 may also be operated to modify the programmed modulation parameters to actively control the characteristics of the electrical modulation energy output by the IPG 127. A clinician may use the CP 129 to program modulation parameters into the IPG 127 and ETM 130 in the operating room and in follow-up sessions.

The CP 129 may indirectly communicate with the IPG 127 or ETM 130, through the RC 128, via an IR communications link 137 or another link. The CP 129 may directly communicate with the IPG 127 or ETM 130 via an RF communications link or other link (not shown). The clinician detailed modulation parameters provided by the CP 129 may also be used to program the RC 128, so that the modulation parameters can be subsequently modified by operation of the RC 128 in a stand-alone mode (i.e., without the assistance of the CP 129). Various devices may function as the CP 129. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 129. Alternatively, such programming methodologies can be performed using firmware or hardware. In any event, the CP 129 may actively control the characteristics of the electrical modulation generated by the IPG 127 to allow the desired parameters to be determined based on patient feedback or other feedback and for subsequently programming the IPG 127 with the desired modulation parameters. To allow the user to perform these functions, the CP 129 may include user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters, including electrode selection, in both a surgical setting and a clinical setting. The display screen(s) may be used to suggest the electrode(s) for use to stimulate a targeted dorsal root. The external device(s) (e.g. CP and/or RC) may be configured to communicate with other device(s), including local device(s) and/or remote device(s). For example, wired and/or wireless communication may be used to communicate between or among the devices.

An external charger 138 may be a portable device used to transcutaneous charge the IPG 127 via a wireless link such as an inductive link 136. Once the IPG 127 has been programmed, and its power source has been charged by the external charger or otherwise replenished, the IPG 127 may function as programmed without the RC 128 or CP 129 being present.

Figures 2, 3A, 3B:
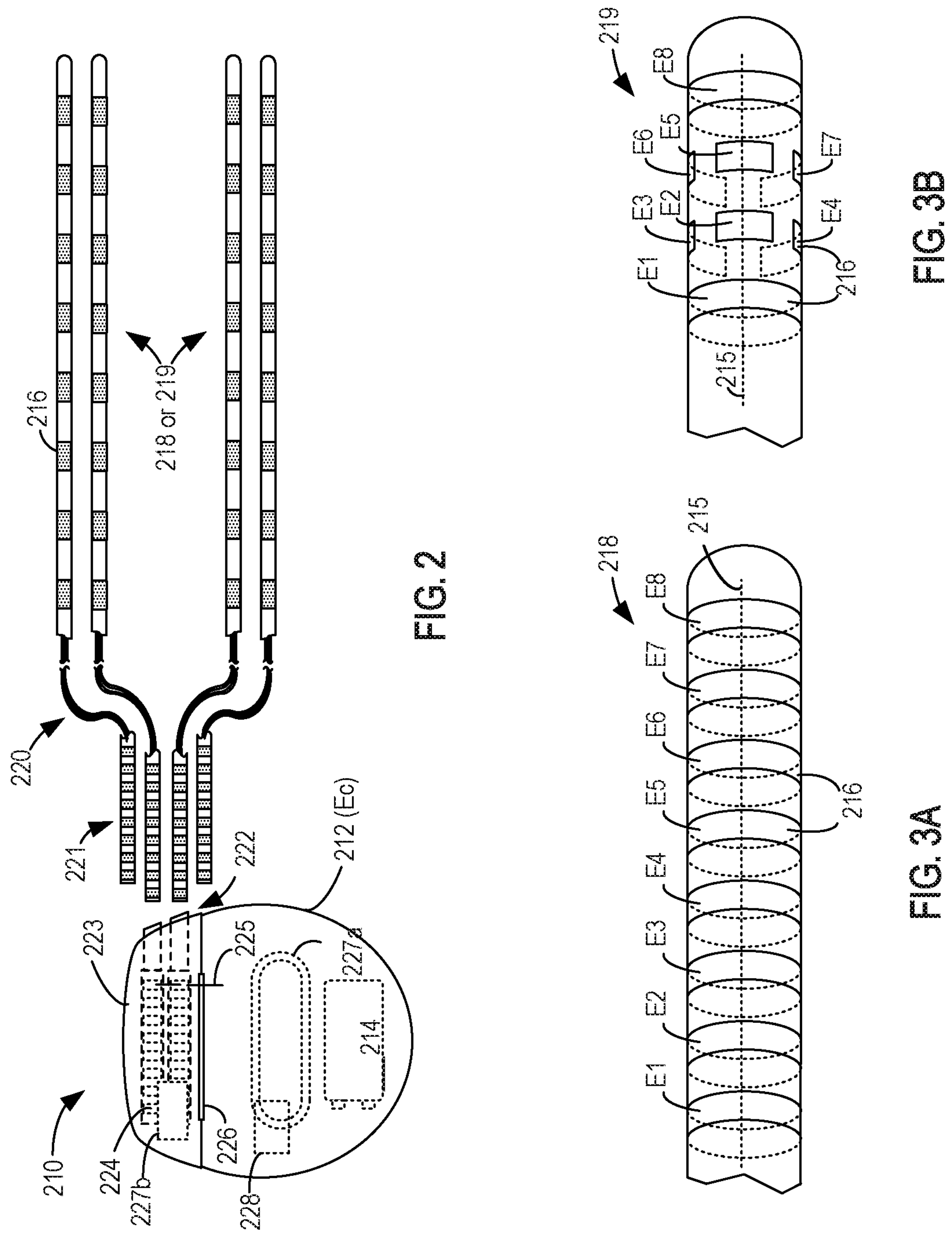
FIG. 2 illustrates an example of an implantable pulse generator (IPG) that may be used in a DBS system.
FIGS. 3A-3B illustrate examples of leads that may be coupled to an IPG to deliver electrostimulation such as DBS.

FIG. 2 illustrates, by way of example and not limitation, an IPG 210 in a DBS system. The IPG 210, which is an example of the IPG 117 of the electrical stimulation system 100 as illustrated in FIG. 1, may include a biocompatible device case 212 that holds the circuitry and a battery 214 for providing power for the IPG 210 to function, although the IPG 210 can also lack a battery and can be wirelessly powered by an external source. The IPG 210 may be coupled to one or more leads, such as leads 218 or 219 as illustrated herein. The lead 218 or 219 can each include a plurality of electrodes 216 for delivering electrostimulation energy, recording electrical signals, or both. In some examples, the leads 218 or 219 can be rotatable so that the electrodes 216 can be aligned with the target neurons after the neurons have been located such as based on the recorded signals.

The leads 218 or 219 can be implanted near or within the desired portion of the body to be modulated. In an example of operations for DBS, access to the desired position in the brain can be accomplished by drilling a hole in the patient's skull or cranium with a cranial drill (commonly referred to as a burr), and coagulating and incising the dura mater, or brain covering. A lead can then be inserted into the cranium and brain tissue with the assistance of a stylet (not shown). The lead can be guided to the target location within the brain using, for example, a stereotactic frame and a microdrive motor system. In some examples, the microdrive motor system can be fully or partially automatic. The microdrive motor system may be configured to perform actions such as inserting, advancing, rotating, or retracing the lead.

Lead body of the leads 218 or 219 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the leads 218 or 219 may be in contact with body tissue for extended periods of time. In some examples, the leads 218 or 219 can have a cross-sectional diameter of no more than 1.5 mm and may be in the range of 0.5 to 1.5 mm.

The electrodes 216 can be made of metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use. The electrodes 216 can include one or more ring electrodes, one or more sets of segmented electrodes (also known as directional electrodes), or a combination of ring electrodes and segmented electrodes, examples of which are discussed below with reference to FIGS. 3A and 3B.

Lead wires 220 within the leads may be coupled to the electrodes 216 and to proximal contacts 221 insertable into lead connectors 222 fixed in a header 223 on the IPG 210, which header can comprise an epoxy for example. Alternatively, the proximal contacts 221 may connect to lead extensions (not shown) which are in turn inserted into the lead connectors 222. Once inserted, the proximal contacts 221 connect to header contacts 224 within the lead connectors 222, which are in turn coupled by feedthrough pins 225 through a case feedthrough 226 to stimulation circuitry 228 within the case 212, which stimulation circuitry 228 is described below.

By way of example and not limitation, the IPG 210 illustrated in FIG. 2 can be coupled to four percutaneous leads 218 or 219 (218 is shown), and thus the header 223 may include a 2×2 array of eight-electrode lead connectors 222. However, the type and number of leads, and the number of electrodes, in an IPG is application specific and therefore can vary. In another example not shown, a given lead can have sixteen electrodes, and thus this lead would have two sets of proximal contacts 221 to mate with two of the eight-electrode lead connectors 222, as disclosed for example in U.S. Patent Application Publication 2019/0076645. The conductive case 212 can also comprise an electrode (Ec).

In a DBS application, as is useful in the treatment of tremor in Parkinson's disease for example, the IPG 210 is typically implanted under the patient's clavicle (collarbone). The leads 218 or 219 (which may be extended by lead extensions, not shown) can be tunneled through and under the neck and the scalp, with the electrodes 216 implanted through holes drilled in the skull and positioned for example in the subthalamic nucleus (STN) and the pedunculopontine nucleus (PPN) in each brain hemisphere. The IPG 210 can also be implanted underneath the scalp closer to the location of the electrodes' implantation. The leads 218 or 219, or the extensions 633, can be integrated with and permanently connected to the IPG 210 in other solutions.

The IPG 210 can include an antenna 227*a* allowing it to communicate bi-directionally with a number of external devices discussed subsequently. The antenna 227*a* as shown comprises a conductive coil within the case 212, although the coil of the antenna 227*a* can also appear in the header 223. When the antenna 227*a* is configured as a coil, communication with external devices preferably occurs using near-field magnetic induction. The IPG 210 may also include a Radiofrequency (RF) antenna 227*b*. Although the RF antenna 227*b* is shown within the header 223, in some examples it may also be within the case 212. The RF antenna 227*b* may comprise a patch, slot, or wire, and may operate as a monopole or dipole. The RF antenna 227*b* preferably communicates using far-field electromagnetic waves, and may operate in accordance with any number of known RF communication standards, such as Bluetooth, Zigbee, WiFi, MICS, and the like. If the IPG 210 lacks a battery 214, an additional coil can be present to receive wireless power from an external source.

Stimulation in IPG 210 is typically provided by pulses each of which may include one phase or multiple phases. For example, a monopolar stimulation current can be delivered between a lead-based electrode (e.g., one of the electrodes 216) and the case electrode Ec 212. A bipolar stimulation current can be delivered between two lead-based electrodes (e.g., two of the electrodes 216). Stimulation parameters typically include current amplitude (or voltage amplitude), frequency, pulse width of the pulses or of its individual phases; electrodes selected to provide the stimulation; polarity of such selected electrodes, i.e., whether they act as anodes that source current to the tissue, or cathodes that sink current from the tissue. Each of the electrodes can either be used (an active electrode) or unused (OFF). When the electrode is used, the electrode can be used as an anode or cathode and carry anodic or cathodic current. In some instances, an electrode might be an anode for a period of time and a cathode for a period of time. These and possibly other stimulation parameters (e.g., frequency, pulse width, amplitude, electrode choice and configuration) taken together comprise a stimulation program that the stimulation circuitry 228 in the IPG 210 can execute to provide therapeutic stimulation to a patient.

In some examples, a measurement device coupled to the muscles or other tissue stimulated by the target neurons, or a unit responsive to the patient or clinician, can be coupled to the IPG 210 or microdrive motor system. The measurement device, user, or clinician can indicate a response by the target muscles or other tissue to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

FIGS. 3A-3B illustrate, by way of example and not limitation, leads 216 and 218 that may be coupled to the IPG 210 to deliver electrostimulation such as DBS. FIG. 3A shows a lead 218 with electrodes 216 disposed at least partially about a circumference of the lead 218. The electrodes 216 may be located along a distal end portion of the lead 218. As illustrated herein, the electrodes 216 are ring electrodes that span 360 degrees about a circumference of the lead 218. A ring electrode allows current to project equally in every direction from the position of the electrode, and typically does not enable stimulus current to be directed from only a particular angular position or a limited angular range around of the lead. The lead 218, which includes only ring electrodes, is also referred to as a non-directional lead.

FIG. 3B shows a lead 219 with electrodes 216 including ring electrodes such as E1 at a proximal end and E8 at the distal end. Additionally, the lead 219 also include a plurality of segmented electrodes (also known as split-ring electrodes). For example, a set of segmented electrodes E2, E3, and E4 are around the circumference at a longitudinal position, each spanning less than 360 degrees around the lead axis. In an example, each of electrodes E2, E3, and E4 spans 90 degrees, with each being separated from the others by gaps of 30 degrees. Another set of segmented electrodes E5, E6, and E7 are located around the circumference at another longitudinal position different from the segmented electrodes E2, E3 and E4. Segmented electrodes such as E2-E7 can direct stimulus current to a selected angular range around the lead.

Segmented electrodes can typically provide superior current steering than ring electrodes because target structures in DBS or other stimulation are not typically symmetric about the axis of the distal electrode array. Instead, a target may be located on one side of a plane running through the axis of the lead. Through the use of a radially segmented electrode array, current steering can be performed not only along a length of the lead but also around a circumference of the lead. This provides precise three-dimensional targeting and delivery of the current stimulus to neural target tissue, while potentially avoiding stimulation of other tissue. In some examples, segmented electrodes can be together with ring electrodes. The lead 219, which include at least one or more segmented electrodes, is also referred to as a directional lead. In an example, all electrodes on a directional lead can be segmented electrodes. In another example, there can be different numbers of segmented electrodes at different longitudinal positions.

As illustrated in FIG. 3B, segmented electrodes may be grouped into sets of segmented electrodes, where each set is disposed around a circumference at a particular longitudinal location of the directional lead 219. The directional lead 219 may have any number (e.g., three as shown in FIG. 3B) segmented electrodes in a given set of segmented electrodes. By way of example and not limitation, a given set may include any number between two to 16 segmented electrodes. In an example, all sets of segmented electrodes may contain the same number of segmented electrodes. In another example, one set of the segmented electrodes may include a different number of electrodes than at least one other set of segmented electrodes.

The segmented electrodes may vary in size and shape. In some examples, the segmented electrodes are all of the same size, shape, diameter, width or area or any combination thereof. In some examples, the segmented electrodes of each circumferential set (or even all segmented electrodes disposed on the directional lead 219) may be identical in size and shape.

Each set of segmented electrodes may be disposed around the circumference of the lead body to form a substantially cylindrical shape around the lead body. The spacing between individual electrodes of a given set of the segmented electrodes may be the same, or different from, the spacing between individual electrodes of another set of segmented electrodes on the directional lead 219. In some examples, equal spaces, gaps or cutouts are disposed between each segmented electrode around the circumference of the directional lead 219. In other examples, the spaces, gaps or cutouts between the segmented electrodes may differ in size or shape. In other examples, the spaces, gaps, or cutouts between segmented electrodes may be uniform for a particular set of the segmented electrodes, or for all sets of the segmented electrodes. The sets of segmented electrodes may be positioned in irregular or regular intervals along a length the directional lead 219.

Figure 4:
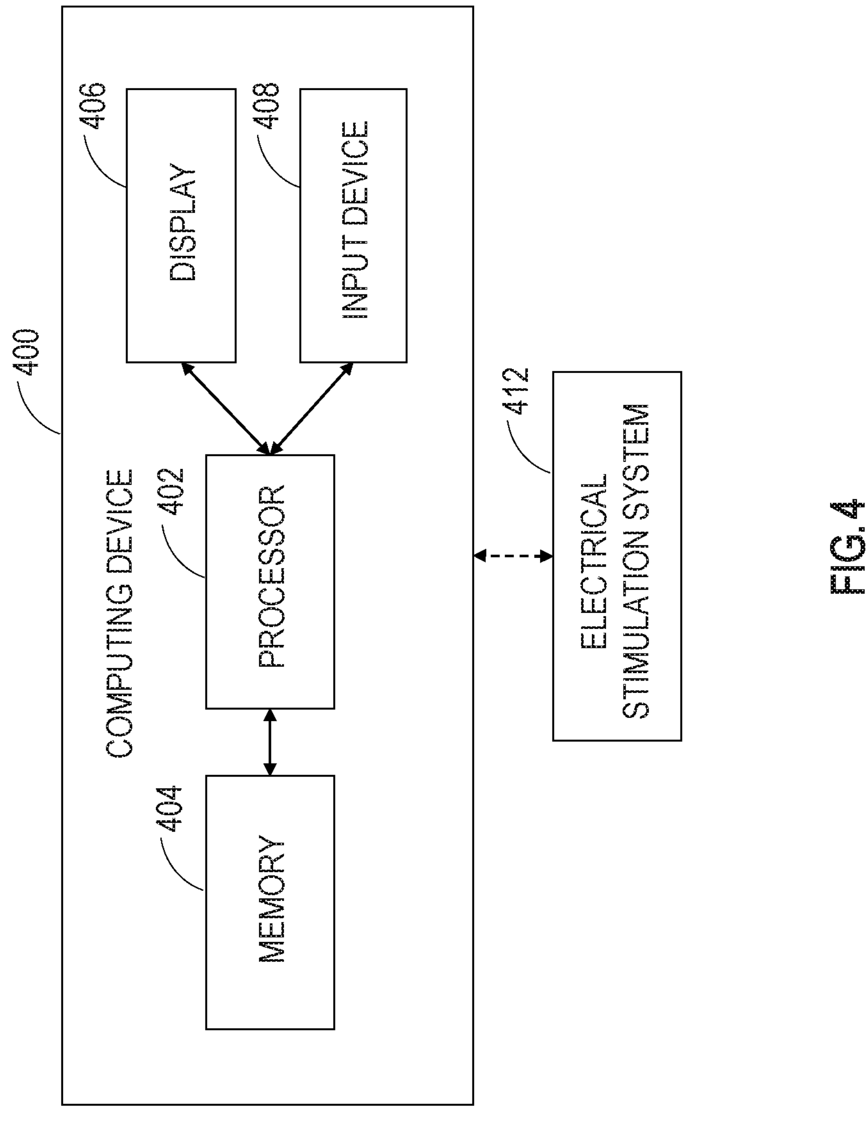
FIG. 4 illustrates an example of a computing device for programming or controlling the operation of an electrostimulation system.

FIG. 4 illustrates, by way of example and not limitation, a computing device 400 for programming or controlling the operation of an electrical stimulation system 412. The computing device 400 includes a processor 402, a memory 404, a display 406, and an input device 408. Optionally, the computing device 400 may be separate from and communicatively coupled to the electrical stimulation system 412. Alternatively, the computing device 400 may be integrated with the electrical stimulation system 412. In an example, the computing device 400 can be a part of the electrical stimulation system 412, such as part of the IPG 127, RC 128, CP 129, or ETM 130 illustrated in FIG. 1.

The computing device 400, also referred to as a programming device, can be a computer, tablet, mobile device, or any other suitable device for processing information. The computing device 400 can be local to the user or can include components that are non-local to the computer including one or both of the processor 402 or memory 404 (or portions thereof). For example, the user may operate a terminal that is connected to a non-local processor or memory. In some examples, the computing device 400 can include a watch, wristband, smartphone, or the like. Such computing devices can wirelessly communicate with the other components of the electrical stimulation system, such as the CP 129, RC 128, ETM 130, or IPG 127 illustrated in FIG. 1. The computing device 400 may be used for gathering patient information, such as general activity level or present queries or tests to the patient to identify or score pain, depression, stimulation effects or side effects, cognitive ability, or the like. In some examples, the computing device 400 may prompt the patient to take a periodic test (for example, every day) for cognitive ability to monitor, for example, Alzheimer's disease. In some examples, the computing device 400 may detect, or otherwise receive as input, patient clinical responses to electrostimulation such as DBS, and determine or update stimulation parameters using a closed-loop algorithm based on the patient clinical responses, as described below with reference to FIG. 5. Examples of the patient clinical responses may include physiological signals (e.g., heart rate, heart sounds, blood pressure), motor parameters (e.g., tremor, rigidity, bradykinesia, eye movements, facial movements, speech), non-motor parameters (e.g., sleep quality or alertness quality), or cognitive parameters indicative of patient cognitive abilities. The computing device 400 may communicate with the CP 129, RC 128, ETM 130, or IPG 127 and direct the changes to the stimulation parameters to one or more of those devices. In some examples, the computing device 400 can be a wearable device used by the patient only during programming sessions. Alternatively, the computing device 400 can be worn all the time and continually or periodically adjust the stimulation parameters. In an example, the closed-loop algorithm for determining or updating stimulation parameters can be implemented in a mobile device (e.g., a smartphone) communicatively connected to the IPG or an evaluating device (e.g. a wristband or watch). These devices can also record and send information to the clinician.

The processor 402 can include one or more processors that may be local to the user or non-local to the user or other components of the computing device 400. In an example, the processor 402 may execute instructions (e.g., stored in the memory 404) to determine a search space of electrode configurations and parameter values, create or update one or more stimulation settings that are selectable for use in electrostimulation therapies such as DBS. In this document, the search space refers to a collection of available electrodes, possible electrode configurations, and possible values or value ranges of one or more stimulation parameters applied to electrodes to deliver electrostimulation. The search space can be specific to a particular lead or a type of lead (such as the non-directional lead 218 or the directional lead 219) with respect to a specific neural target. As a result, different search spaces may be determined for different leads or types of lead and/or for different neural targets. A stimulation setting includes an electrode configuration and values for one or more stimulation parameters. The electrode configuration may include information about electrodes (ring electrodes and/or segmented electrodes) selected to be active for delivering stimulation (ON) or inactive (OFF), polarity of the selected electrodes, electrode locations (e.g., longitudinal positions of ring electrodes along the length of a lead, or longitudinal positions and angular positions segmented electrodes on a circumference at a longitudinal position of the lead), stimulation modes such as monopolar pacing or bipolar pacing, etc. The stimulation parameters may include, for example, current amplitude values, current fractionalization across electrodes, stimulation frequency, stimulation pulse width, etc.

The processor 402 may identify or modify a stimulation setting from the search space through an optimization process until a search criterion is satisfied, such as until an optimal, desired, or acceptable patient clinical response is achieved. In an example, the processor 402 may identify a first set of base stimulation settings and a different second set of base stimulation settings. Each base stimulation setting of the first and second sets comprises an electrode configuration and stimulation parameter values or value ranges selected from the search space. For a base stimulation setting of the first set, electrostimulation programmed with said base setting can be delivered to the patient, clinical effects (including therapeutic effects and/or side effects, or motor symptoms such as bradykinesia, tremor, or rigidity) may be detected, and a clinical response be evaluated based on the detected clinical effects. Because actual electrostimulation is administered, the base stimulation settings of the first set are referred to as tested base stimulation settings, and the clinical responses are referred to as tested clinical responses. In contrast, for a base stimulation setting of the second set, no electrostimulation is delivered to the patient; instead, clinical effects may be predicted using a computational model based on the clinical effects detected from the electrostimulation testing based on the first set of base stimulation settings, and a clinical response may be estimated using the predicted clinical effects. Because no electrostimulation is delivered, the base stimulation settings of the second set are referred to as predicted or estimated base stimulation settings, and the clinical responses are referred to as predicted or estimated clinical responses. Examples of identifying the first and second sets of stimulation settings, and providing electrostimulation therapy in accordance with such an identified stimulation settings, are discussed below with reference to FIG. 5.

The processor 402 may determine one or more characteristic stimulation amplitudes for an electrode configuration in the search space, such as for an electrode configuration of a base stimulation setting of a first set, or an electrode configuration of a base stimulation setting of a second set. The characteristic stimulation amplitudes each correspond to respective clinical response indicators or clinical effects satisfying respective conditions. The characteristic stimulation amplitudes can be determined based on the clinical response indicators of the first and second sets of base stimulation settings. In some examples, characteristic stimulation amplitudes can be determined for each of a range of electrodes on a lead, such as ring electrodes on the non-directional lead 218, or segmented electrodes on the directional lead 219. The processor 402 can further generate a formatted report including the characteristic stimulation amplitudes for one or more electrodes or electrode configurations, optionally along with the clinical response data of the first and second sets of base stimulation settings. The formatted report can be presented to a system user (e.g., a physician) to assist programming of electrostimulation such as DBS. Examples of generating characteristic stimulation amplitudes and presenting a formatted report are discussed below with reference to FIGS. 8-9.

In various examples, portions of the functions of the processor 402 may be implemented as a part of a microprocessor circuit. The microprocessor circuit can be a dedicated processor such as a digital signal processor, application specific integrated circuit (ASIC), microprocessor, or other type of processor for processing information. Alternatively, the microprocessor circuit can be a processor that can receive and execute a set of instructions of performing the functions, methods, or techniques described herein.

The memory 404 can store instructions executable by the processor 402 to perform varies functions including, for example, determining a reduced or restricted electrode configuration and parameter search space (also referred to as a "restricted search space"), creating or modifying one or more stimulation settings within the restricted search space, etc. The memory 404 may store the search space, and one or more stimulation programs each including respective stimulation settings each associated with respective optimization criteria such as clinical response indicators, as to be discussed with reference to FIG. 5.

The memory 404 can be a computer-readable storage media that includes, for example, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information, and which can be accessed by a computing device. In some examples, the memory 404 can be a cloud storage.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, Bluetooth™, near field communication, and other wireless media.

The display 406 can be any suitable display or presentation device, such as a monitor, screen, display, or the like, and can include a printer. The display 406 can be a part of a user interface configured to display information about stimulation settings (e.g., electrode configurations and stimulation parameter values and value ranges) and user control elements for programming a stimulation setting into an IPG. In some examples, the user interface may include a speaker that provides audio information about stimulation settings, and receive audio input from the user, such as a clinician or the patient.

The input device 408 can be, for example, a keyboard, mouse, touch screen, track ball, joystick, voice recognition system, or any combination thereof, or the like. Another input device 408 can be a camera from which the clinician can observe the patient. Yet another input device 408 is a microphone where the patient or clinician can provide responses or queries.

The electrical stimulation system 412 can include, for example, any of the components illustrated in FIG. 1. The electrical stimulation system 412 may communicate with the computing device 400 through a wired or wireless connection or, alternatively or additionally, a user can provide information between the electrical stimulation system 412 and the computing device 400 using a computer-readable medium or by some other mechanism. As mentioned, in some examples, the computing device 400 may include part of the electrical stimulation system, such as, for example, the IPG 127, RC 128, CP 129, or ETM 130 or any combination thereof.

Figure 5:
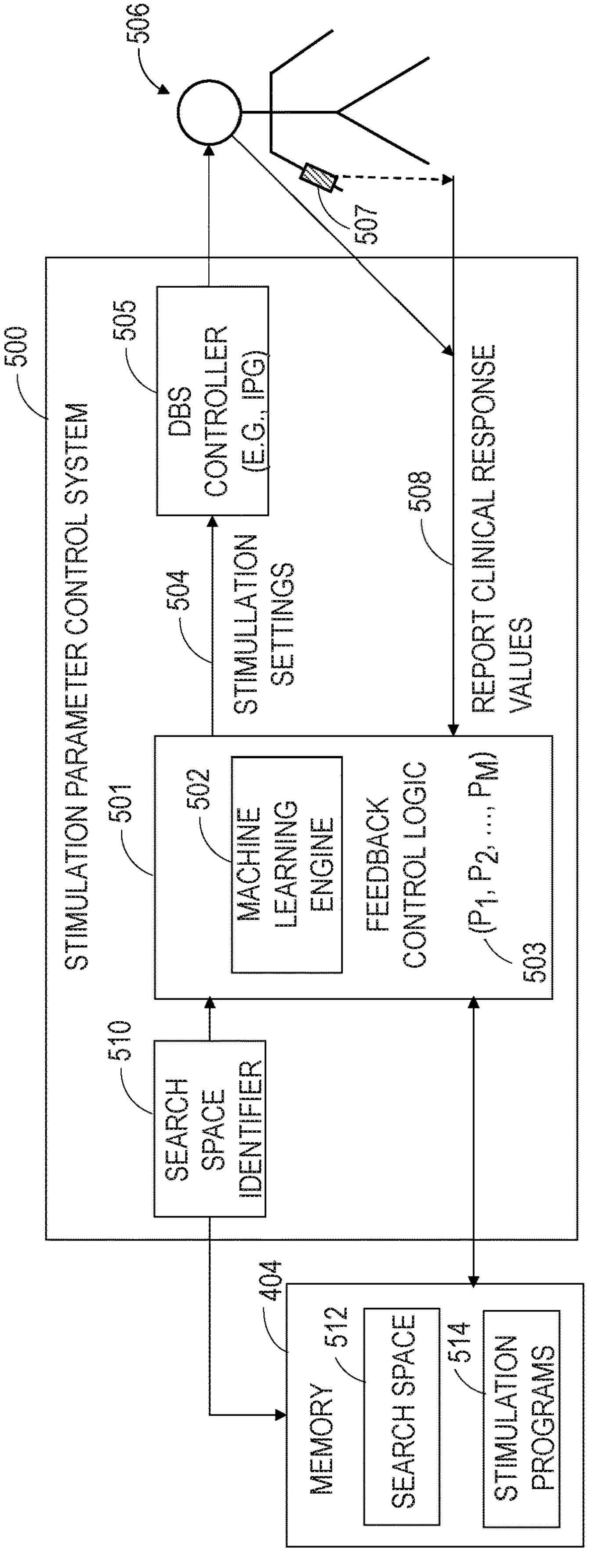
FIG. 5 illustrates an example of a stimulation parameter control system and a part of the environment in which it may operate.

FIG. 5 illustrates, by way of example and not limitation, a stimulation parameter control system 500 and a part of the environment in which it may operate. The stimulation parameter control system 500, which may be implemented as a part of the processor 402, may include a feedback control logic 501, a DBS controller 505, and a search space identifier 510. The feedback control logic 501 may be implemented in, for example, the CP 129 or the RC 128. The feedback control logic 501 can determine or modify one or more stimulation settings 504 for a stimulation lead (such as leads 218 or 219) at target stimulation region, such as a region in a brain hemisphere. A stimulation setting includes electrode configuration and values for one or more stimulation parameters ($P_1$, $P_2$, . . . , $P_m$) 503. The electrode configuration includes information about electrodes (ring electrodes and/or segmented electrodes) selected to be active for delivering stimulation (ON) or inactive (OFF), polarity of the selected electrodes, electrode locations (also referred to as contact locations, which may include longitudinal positions of ring electrodes along the length of a lead, or angular positions of segmented electrodes about a circumference at a longitudinal position of the lead), stimulation modes such as monopolar pacing or bipolar pacing, etc. The stimulation parameters may include, for example, current amplitude values, current fractionalization across electrodes, stimulation frequency, stimulation pulse width, etc. In some examples, the feedback control logic 501 may modify the stimulation setting 504 such as by changing a stimulation parameter value, or modifying an electrode configuration.

The stimulation setting 504 may be provided to the DBS controller 505 to configure the IPG 127 or ETM 130 to deliver DBS therapy to the patient 506 in accordance with the stimulation setting or the modified stimulation setting. The stimulation may produce certain therapeutic effects and/or side effects on the patient 506. Such therapeutic effectiveness and side effects, also referred to as clinical responses or clinical metrics, may be provided to the feedback control logic 501. In an example, the clinical responses may be based on patient or clinician observations. For example, motor symptoms such as bradykinesia (slowness of movement), rigidity, tremor, among other symptoms or side effects, can be scored by the patient or by the clinician upon overserving or questioning the patient. In some examples, the clinical responses can be objective in nature, such as measurements automatically or semi-automatically taken by a sensor 507. In an example, the sensor 507 may be included in a wearable device associated with patient 506, such as a smart watch. For example, a Parkinson's patient may be fitted with a wearable sensor that measures tremors, such as by measuring the frequency and amplitude of such tremors. U.S. patent application Ser. No. 17/137,110, filed Dec. 29, 2020, which is incorporated herein by reference in its entirety, discusses determining which symptoms and/or side effects are most sensible to score for a given patient when the stimulation parameters are optimized.

The clinical responses, either reported by the patient or measured by a sensor, may be converted to clinical response values 508, also referred to as clinical response scores. In an example, the clinical response values 508 may be computed based on the intensity, frequency, or duration of one or more of tremor, rigidity, or bradykinesia responses. Based upon the received clinical response values 508, the feedback control logic 501 can adjust electrode configurations or values of one or more stimulation parameters 503. The feedback control logic 501 can send the adjusted (new or revised) stimulation setting 504, such as the electrode configuration or the adjusted stimulation parameter values, to further configure the DBS controller 505 to change the stimulation parameters of the leads implanted in patient 506 to the adjusted values.

The feedback-control loop as illustrated in FIG. 5 can continue until an optimal, desired, or acceptable outcome is reached, such as maximizing therapeutic effectiveness while minimizing unwanted side effects, or until a specific stop condition is reached such as number of iterations, time spent in programming session, or the like. An outcome may be considered optimal, desired, or acceptable if it meets certain threshold values or tests (e.g., improved clinical response for the patient, faster programming of the device, increased battery life, and/or control multiple independent current sources and directional lead). Such an iterative process of looking for a stimulation setting (e.g., an electrode configuration and stimulation parameter values for the electrode) is referred to as a stimulation setting optimization process. The outcome being reached is referred to as an optimization criterion, and the resultant stimulation setting is referred to as an optimal base stimulation setting (BSS). By way of example and not limitation, the optimization criterion may include possible optimal clinical outcome within the parameters chosen; time spent, iterations taken, or power usage to explore the search space until a desired clinical outcome is reached (assuming multiple outcomes with the same or comparable clinical response); among others.

In an example, the optimization criterion includes the clinical response values 508 exceeding a threshold value or falling into a specified value range, indicating a satisfactory therapeutic outcome has reached. Depending on how the clinical response values are computed, one or more optimal base stimulation settings may be determined. For example, the clinical response values may be computed using a single response effect (e.g., one of bradykinesia, tremor, or rigidity). Accordingly, three optimal base stimulation settings may be generated: a first optimal base stimulation setting ($BSS_1$) corresponding to a bradykinesia score exceeding a threshold, a second optimal base stimulation setting ($BSS_2$) corresponding to a tremor score exceeding a threshold, and a third optimal base stimulation setting ($BSS_3$) corresponding to a rigidity score exceeding a threshold. In another example, the clinical response values can be a composite score computed as a weighted combination of multiple clinical effects, such as a %*bradykinesia+b %*tremor+c %*rigidity. Accordingly, a fourth optimal base stimulation setting ($BSS_4$) can be generated, corresponding to the composite clinical response score exceeding a threshold. In some examples, the stimulation setting optimization can be performed in an in-clinic testing and programming session such during implantation or revision of a DBS system or device follow-up, where a clinician may use a graphical user interface (GUI) interacting with the feedback control logic 501 to generate one or more optimal base stimulation settings, as discussed below with reference to FIG. 6.

The optimal base stimulation settings (e.g., $BSS_1$ through $BSS_4$), may be stored in the memory 404. In an example, a stimulation setting, along with the corresponding unique clinical response indicator (e.g., weighted combination of clinical effects with unique weight factors) form a stimulation program 514, which can also be stored in the memory 404. Each stimulation programmed can be associated with, or tagged by, one or more unique clinical response indicators.

In some examples, the clinical response values 508 may be weighted according to the time at which the test took place. It has been found that, for at least some patients or at least some testing procedures, patient fatigue occurs over time which may degrade or otherwise change the clinical response values (whether obtained from the patient, clinician, or a sensor). For example, more recent clinical response values 508 may be weighted higher than earlier clinical response values as the more recent clinical response values are more predictive of the clinical response to the adjusted stimulation parameters because these later tests have a similar amount of patient fatigue. In some cases, the clinical response values may be affected by circadian (e.g., day and night) cycles or medication usage. By way of example and not limitation, the weights can be in a range from 1.05 to 1.5.

In various examples, the stimulation parameter control system 500 may be executed on its own and is not connected to a controller. In such instances it may be used to merely determine and suggest programming parameters, visualize a parameter space, test potential parameters, etc.

The process of iterative search for a stimulation setting (e.g., an electrode configuration and/or stimulation parameter values) typically involves significant computation and time, especially when electrode configuration involves segmented electrodes in a directional lead (e.g., lead 219). If testing all possible settings in the entire parameter space (including electrode configurations and combinations of stimulation parameter values) is done as comprehensively as possible, stimulation would need to be provided to the patient for each possible setting, which may end up with a burdensome and time-consuming programming session. Because practically a programming session may only last a few hours, only a fraction of possible electrode configuration and stimulation parameter combinations can reasonably be tested and evaluated. To reduce the time taken and to improve the efficiency of stimulation setting optimization process, a reduced or restricted electrode configuration and parameter search space can be used. By applying limitations or constraints to the electrode configurations and parameter values, the restricted search space can include a subset of electrodes (e.g., a subset of ring electrodes and/or a subset of segmented electrodes on a lead) that are selected as active electrodes for delivering stimulation, and values or value ranges for one or more stimulation parameters (e.g., a range of current amplitude ranges for an active electrode). Stimulation setting optimization, when performed within such a search space, can be more efficient and cost-effective than searching through the entire parameter space for one or more optimal base stimulation settings such as $BSS_1$-$BSS_4$ as discussed above.

The search space identifier 510 can automatically determine a search space 512 for a stimulation lead (e.g., the non-directional lead 218 or the directional lead 219) at a neural target, such as a region in a brain hemisphere, by imposing certain limitations or constraints on the electrode configurations and/or parameter values or value ranges. In an example, the search space 512 can be determined based on spatial information of the lead, such as lead positions with respect to neural targets, which can be obtained from imaging data of the lead and patient anatomy. Additionally or alternatively, the search space 512 can be determined based on physiological information such as physiological signals sensed by the electrodes at their respective tissue contact locations. The physiological information may include patient clinical responses to stimulation. In some examples, prior knowledge about patient medical condition, health status, DBS treatment history may also be utilized to determine the search space 512. In an example, the search space identifier 510 may exclude those electrodes on the lead that are out of a region of interest, such that the search space includes only those electrodes within the target of interest. One or more stimulation parameters may be restricted to take certain values or within value ranges. For example, the restricted search space may include certain electrode positions and value ranges for stimulation current amplitude, frequency, or pulse width. The feedback control logic 501 can determine one or more optimal base stimulation settings (e.g., $BSS_1$-$BSS_4$) by searching through the identified search space 512. The identified search space 512 can be stored in the memory 404. Commonly assigned U.S. Patent Application Ser. No. 63/186,596, filed May 10, 2021, discusses determining a search space and adjusting electrode configuration and/or parameter values within the search space, the disclosure of which is hereby incorporated by reference in its entirety. Commonly assigned U.S. Patent Application Ser. No. 63/186,590, filed May 10, 2021, discusses reducing neurostimulation electrode configuration and parameter search space based on electrode position information relative to an anatomical region of interest or physiological signals sensed by the plurality of electrodes, and determining a target stimulation setting based on patient clinical responses, the disclosure of which is hereby incorporated by reference in its entirety.)

The feedback control logic 501 may include a machine learning engine 502 that can facilitate the stimulation parameter control system 500 (or a user of the system) to explore the search space in order to choose values for programming the DBS controller 505. The machine learning engine 502 can employ supervised or unsupervised learning algorithms to train a prediction model, and use the trained prediction model to predict patient clinical responses to an untested stimulation setting (e.g., untested stimulation parameter values or untested electrode configurations), or to estimate or predict stimulation parameters values or electrode configurations that, when provided to the DBS controller 505 to deliver stimulation accordingly to the patient 506, would produce desired or improved clinical responses. Examples of the learning algorithms include, for example, Naive Bayes classifiers, support vector machines (SVMs), ensemble classifiers, neural networks, Kalman filters, regression analyzers, etc. The machine learning engine 502 can build and train a prediction model using training data, such as stimulation parameter values and corresponding patient clinical responses. The training date can be acquired from a training session such as performed in a clinic. Additionally or alternatively, the training data can be obtained from historical data acquired by the stimulation parameter control system 500. With its learning and prediction capability, the machine learning engine 502 can aid a user (e.g., a clinician) in exploring the stimulation parameter space more effectively and more efficiently to produce results that are optimal, desired, or acceptable.

In some examples, the machine learning engine 502 can utilize imaging data to inform the choice of the next set of values. This will be particularly useful, when the algorithm finds itself in a region of parameter space for which the clinical responses are not substantially affected by the changes in the stimulation parameters, and the choice of next step is not apparent from the patient response alone. Imaging data that provides information about the location of the lead in the patient's brain along with priors informing the algorithm of which directions may be better choices for the next step could lead to faster convergence.

In some examples, the machine learning engine 502 can determine expected outcomes for parameter values that have not yet been tested based upon what the machine learning engine 502 has "learned" thus far, and provide a recommendation for a next set of values to test. Here, testing refers to the iterative testing required to find an optimal stimulation setting for configuring the DBS controller 505. The recommendation for a next set of values to test is based upon which of the determined expected outcomes meet a set of designated (determined, selected, preselected, etc.) criteria (e.g., rules, heuristics, factors, and the like). For example, rules considered may include such factors as: the next set of values cannot be one of the last 10 settings tested or cannot be too close to previously tested setting. Accordingly, the feedback control logic 501 with its machine learning engine 502 is used to systematically explore the stimulation parameter space based upon what it has learned thus far and (optionally) different rules and/or heuristics that contribute to achieving optimal outcomes more efficiently.

The process for determining expected outcomes for parameter values that have not yet been tested may involve use of other data for machine learning. For example, data from other programming sessions for the same patient as well as from other patients may be used to train the machine learning engine 502. In some examples, no prior data may be used. In this case, the machine learning engine 502 may use data learned from this patient only in one particular setting. In other examples, data from the same patient but from previous sessions may be used. In some examples all patient data from all sessions may be used. In some examples all patient data utilizing lead location information (knowledge of lead location in space relative to anatomy) may be used. Different other combinations are also possible.

In order to use this data for machine learning purposes, the data may first be cleansed, optionally transformed, and then modeled. In some examples, new variables are derived, such as for use with directional leads, including central point of stimulation, maximum radius, spread of stimulation field, or the like. Data cleansing and transformation techniques such as missing data imputation and dimension reduction may be employed to prepare the data for modeling.

The machine learning engine 502 may determine how best a predicted outcome meets the optimal outcome metrics. Various optimization techniques may be used, examples of which may include but are not limited to: optimization algorithms and estimation procedures used to fit the model to the data (e.g., gradient descent, Kalman filter, Markov chain, Monte Carlo, and the like); optimization algorithms reformulated for search (e.g., simulated annealing); spatial interpolation (e.g., kriging, inverse distance weighting, natural neighbor, etc.); supplementary methods that aid the optimization process (e.g., variable selections, regularization, cross validation, etc.); other search algorithms (e.g., golden-section search, binary search, etc.). Using any of these techniques, the machine learning engine 502 can decide whether a particular predicted outcome for a set of stimulation parameter values is the fastest sufficing outcome, the best possible clinical outcome, or the optimal outcome with least battery usage, for example.

The feedback control logic 501 may be used to search and configure different types of stimulation parameters of the various leads potentially causing different clinical effects upon the patient 506. Examples of the stimulation parameters may include electrode configurations (electrode selection, polarities, monopolar or bipolar modes of stimulation), current fractionalization, current amplitude, pulse width, frequency, among others. Given these possible stimulation parameters, the stimulation parameter control system 500 can move about the parameter space in different orders, by different increments, and limited to specific ranges. In some examples, the stimulation parameter control system 500 may allow the user to provide search range limitations to one or more of the stimulation parameters to limit the range for that stimulation parameter over which the system will search for parameters. For example, the user may restrict which electrodes can be used for stimulation or may restrict the amplitude or pulse width to a certain range or with a selected maximum or minimum. As one illustration, based on the site of implantation, the user may be aware that the distal-most and proximal-most electrodes are unlikely to produce suitable stimulation and the user limits the range of electrodes to exclude these two electrodes.

For a lead with segmented electrodes, the number of possibilities for parameter selection can be very large when combinations of electrodes and different amplitudes on each electrode are possible. In some examples using a lead with segmented electrodes, the selection of electrodes used for stimulation may be limited to fully directional selections (i.e., selection of only a single segmented electrode) and fully concentric selections (i.e., all electrodes in a single set of segmented electrodes are active with the same amplitude). In other examples, the initial movement through parameter space may be limited to fully directional and fully concentric selections. After a set of stimulation parameters is identified using these limits, variation in the selection of electrodes may be opened up to other possibilities near the selection in the identified set of stimulation parameters to further optimize the stimulation parameters.

In some examples, the number of stimulation parameters that are varied and the range of those variations may be limited. For example, some stimulation parameters (e.g., electrode selection, amplitude, and pulse width) may have larger effects when varied than other stimulation parameters (e.g., pulse shape or pulse duration). The movement through stimulation parameter space may be limited to those stimulation parameters which exhibit larger effects. In some examples, as the stimulation parameter control system 500 proceeds through testing of sets of stimulation parameters, the system may observe which stimulation parameters provide larger effects when varied and focus on exploring variation in those stimulation parameters.

In some examples, the stimulation parameter control system 500 can include a user interface for visualizing exploration of the stimulation parameter space as the system determines new and better parameter values to test until a solution is determined that fits within certain designated thresholds or a stop condition is reached. In some examples of the stimulation parameter control system 500, the user interface is part of the feedback control logic 501. In other examples, the user interface may be part of another computing system that is part of the stimulation parameter control system 500 or may be remote and communicatively connected to the stimulation parameter control system 500. The user interface may present to a user (such as a clinician, physician, programmer, etc.) a visualization of the predicted expected outcomes for (some of) the stimulation parameter values not yet tested and a recommendation for the next set of stimulation parameter values to test.

In some examples where a deep brain stimulator is configured via the DBS controller 505 with at least one set of stimulation parameter values forwarded by the feedback control logic 501, the clinician may monitor the patient throughout the process and record clinical observables in addition to the patient 506 being able to report side effects. When a side effect is observed, the various search algorithms will take that fact into account when selecting/suggesting a next set of values to test. In some examples, for example, those that select contacts via monopolar review, other parameters may be changed until they cause a side effect, which case is noted as a boundary. For example, in monopolar review where amplitude is another stimulation parameter being varied, the amplitude may be increased progressively until a side-effect is observed.

In some examples, more than one clinical metric (e.g., tremor, rigidity, bradykinesia, etc.) may be important observables. Different examples of the stimulation parameter control system 500 may handle these metrics differently. For example, some examples might identify an ideal location for each metric and choose one ideal location between them, set in the patient's remote controller so the patient can choose as needed, or chose a best combined outcome. As another example, some examples may search multiple outcomes at the same time and use the best combined score as the best outcome or find a best location for each metric individually. As yet another example, some examples may use a sequential process for selecting stimulation parameter values for multiple outcomes. For example, a system may search parameter space for a first outcome (e.g., bradykinesia) and, upon finding a suitable end condition, then search parameter space for a second outcome (e.g., rigidity). While searching parameter space for the first outcome, clinical response values for both the first and second outcomes can be obtained. Thus, when the system switches to the second outcome there are already a number of clinical response values for that outcome which will likely reduce the length of the search.

In some examples, two stimulation leads may be implanted to produce stimulation effects on two sides of the body (e.g., the right and left sides of the body). The same procedure described herein can be used to either jointly determine the stimulation parameters for the two leads by exploring the joint parameter space or individually determine stimulation parameters for the two leads by exploring the parameter space for each lead individually. In some examples, the user may determine for each side of the body which clinical response is dominant or most responsive. This may be done, for example, by having the patient perform a single task which captures multiple responses (e.g. connecting dots on the screen to monitor tremor and bradykinesia of the movement) or a small series of tasks. This enables the system to determine which clinical response to use to identify the stimulation parameters for that side of the body.

As noted, the feedback may be provided directly by the patient 506, entered by an observer such as a clinician (not shown), or may be provided by means of a sensor 507 associated with and in physical, auditory, or visual contact with the patient 506. In an example, the sensor 507 may be included in a wearable device associated with patient 506, such as a smart watch. In an example where the feedback can be monitored automatically or semi-automatically, such as with use of sensor 507, it may not be necessary for a clinician or other observer to be present to operate the stimulation parameter control system 500. Accordingly, in such examples a user interface may not be present in system 500.

In some examples, the stimulation parameter control system 500 may determine one or more optimal base stimulation settings using predicted clinical responses for untested stimulation parameter values or untested electrode configurations without actually delivering stimulation. Such base stimulation settings are referred to as "estimated" base stimulation settings, to distinguish from the "tested" base stimulation settings (e.g., $BSS_1$-$BSS_4$) that are based on the tested clinical response (either reported by the patient or measured by a sensor) to actually delivered stimulation. For examples, based on the "tested" base stimulation settings $BSS_1$-$BSS_4$, the stimulation parameter control system 500 may estimate an optimal base stimulation setting associated with a composite clinical response defined as x %*bradykinesia+y %*tremor+z %*rigidity, or simply denoted by the weight factors (x %, y %, z %). By way of example and not limitation, the stimulation parameter control system 500 may generate a fifth optimal base stimulation setting ($BSS_5$) corresponding to a composite clinical response using bradykinesia and tremor only, each weighted 50%; a sixth optimal base stimulation setting ($BSS_6$) corresponding to a composite clinical response using tremor and rigidity only, each weighted 50%; a seventh optimal base stimulation setting ($BSS_7$) corresponding to a composite clinical response using bradykinesia and rigidity only, each weighted 50%; or an eighth optimal base stimulation setting ($BSS_8$) corresponding to a composite clinical response using bradykinesia, tremor, and rigidity weighted 40%, 40%, and 20%, respectively. Similar to the "tested" base stimulation settings $BSS_1$-$BSS_4$, the "estimated" base stimulation settings $BSS_5$-$BSS_8$, associated with their respective clinical response indicators (e.g., weight factors for clinical effects), can be stored in the memory 404 as respective stimulation programs 514. In an example, the stimulation programs 514 may be stored in a lookup table, where each tested or estimated base stimulation setting (e.g., $BSS_1$ through $BSS_8$) is tagged by respective clinical response indicators or weight factors for clinical effects. In an example, the memory 404 can be a part of memory circuitry internal to the IPG (e.g., IPG 127 or IPG 210). The RC 128 or the CP 129 can request access to the memory 404 to retrieve therefrom one or more stored stimulation programs 514 or the search space 512.

Figure 6:
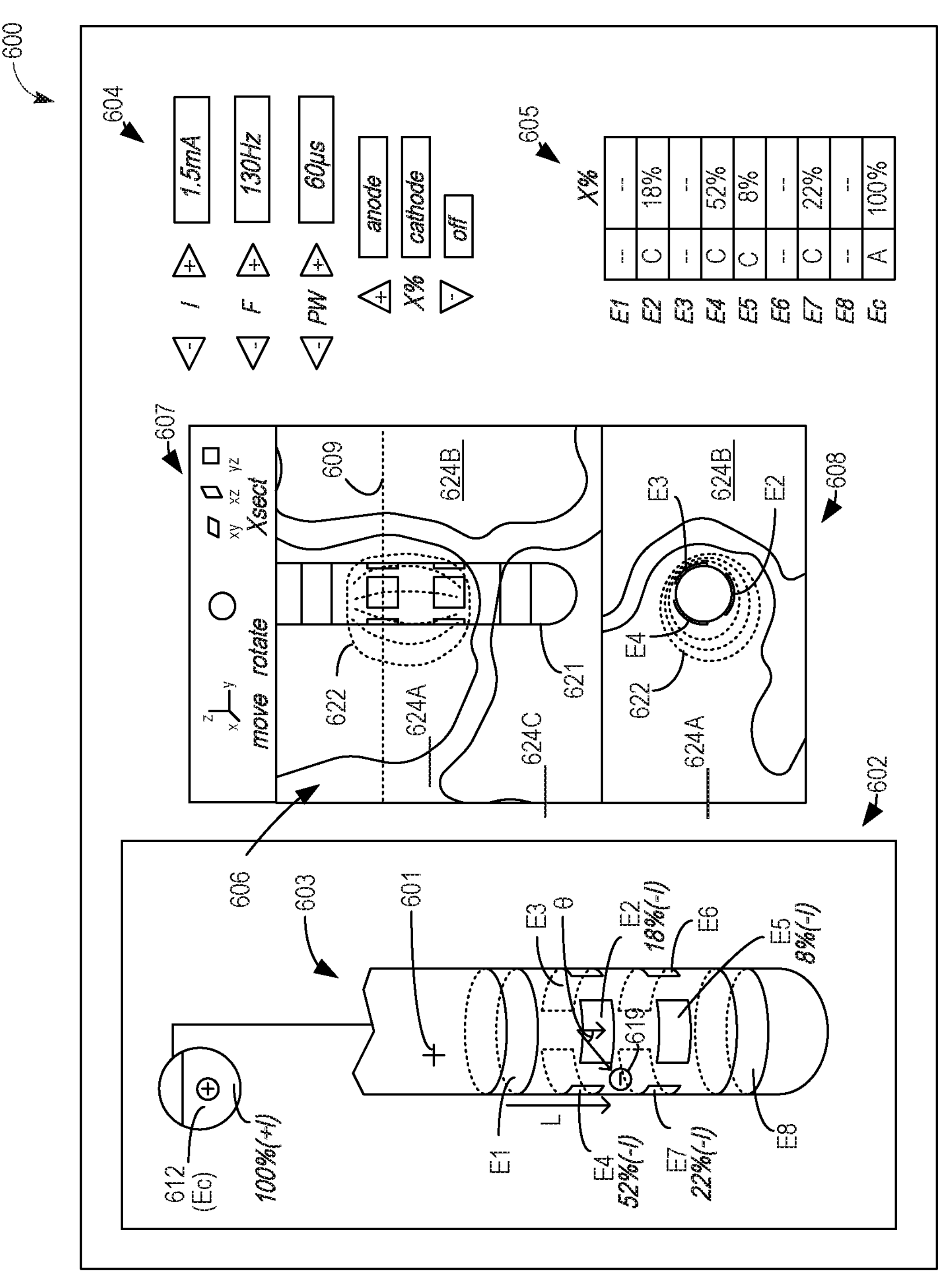
FIG. 6 illustrates an example of a graphical user interface (GUI) for programming a stimulation setting into an IPG.

FIG. 6 illustrates, by way of example and not limitation, a graphical user interface (GUI) 600 operable on an external device such as the clinician program (CP) 129, which allows a user (e.g., a clinician) to program a stimulation setting into the IPG (e.g., IPG 127 or IPG 210). The GUI 600 can be rendered on a display of the CP 129, and provide a clinician with a visual indication of how a stimulation setting (e.g., electrode configuration and/or values for a plurality of stimulation parameters) may interact with target tissue (e.g., brain tissue in the context of DBS) in which the electrodes are implanted. The GUI 600 may be used during surgical implantation of the leads 218 or 219 and the IPG 210, but may also be used after implantation to assist in creating, modifying, or selecting a therapeutically useful stimulation program for the patient.

The GUI 600 can be controlled by a cursor 601 that the user can move using a tracking device such as a mouse connected to the CP 129. The GUI 600 may include a stimulation waveform interface 604 that can display an externally created stimulation waveform, and allow a user to select, and adjust a value of a stimulation waveform parameter, such as a stimulation amplitude (e.g., a current I), a frequency (F), or a pulse width (PW) of stimulation pulses. In some examples, the waveform interface 604 can be significantly more complicated, particularly if the IPG 210 supports the provision of stimulation that is more complicated than a repeating sequence of pulses. In some examples, the waveform interface 604 may allow a user to select biphasic or monophasic pulses, and to select whether passive charge recovery will be used (not shown).

The GUI 600 may include an electrode configuration interface 605 which allows the user to select and modify a particular electrode configuration, such as specifying which electrodes are active electrodes (ON) to provide stimulation, and which electrodes are inactive electrodes (OFF) to refrain from providing stimulation. For an active electrode, the user may also use the electrode configuration interface 605 to specific polarity and relative magnitude for that active electrode. As illustrated in FIG. 6, the user may use the electrode configuration interface 605 to designate an electrode as an anode (A), a cathode (C), or an inactive electrode (OFF), and to specific an amount of the total anodic or cathodic current +I or −I (specified in the waveform interface 604) that a selected active electrode will receive in a form of fraction or percentage (X %) of the total current provided. Such a split of current among multiple electrodes is referred to as current fractionalization. In an example as illustrated in FIG. 6, the case electrode 612 (Ec) is specified as the only anode that receives 100% of anodic current +I. The corresponding cathodic current −I is split among a set of selected active cathode electrodes including E2 (18% of −I), E4 (52% of −I), E5 (8% of −I), and E7 (22% of −I). One or more electrodes can be chosen to act as anodes or cathodes at a given time, allowing the electric field in the tissue to be shaped. Once the stimulation waveform interface 604 and electrode configuration interface 605 are determined, they can be sent to the IPG 210, which can produce stimulation pulses accordingly, and deliver the stimulation pulses to the patient.

The GUI 600 can include a leads interface 602 showing an image 603 of the lead being used for the patient. By way of example and not limitation, the lead shown in the image 603 includes two ring electrodes E1 and E8, a first group of segmented electrodes E2-E4 about a circumference of a first longitudinal position of the lead, and a second group of segmented electrodes E5-E7 about a circumference of a second longitudinal position of the lead. In this example, segmented electrodes E2, E4, E5, and E7 are selected as cathodes to receive fractionalized current. Such current fractionalization sets a particular position for a cathode pole 619 in a three-dimensional space. The position of this cathode pole 619 can be quantified at a particular longitudinal position L along the lead (e.g., relative to a point on the lead such as the longitudinal position of electrode E1). If a direction lead is used, the position of the cathode pole 619 may further be quantified at a particular rotational angle θ (e.g., relative to a particular angle on the lead such as relative to the center of electrode E2). The position (L, θ) of the cathode pole 619, as shown in the leads interface 602, may be virtual; that is, the position may not necessarily be at a physical position of any electrode on the lead, but a point in the three-dimensional space of the leads interface 602. In some examples, the interface 602 can include a selection to access a library of images 603 of the types of leads (e.g., the non-directional lead 218 or the directional lead 219) that may be implanted in different patients, which may be stored with the CP 129. The cursor 601 can be used to select an electrode such as any of E1-E8, or the case electrode Ec, or a pole such as cathode pole 619.

The CP 129 can include and execute an electrode configuration algorithm to determine a position of the cathode pole 619 in the three-dimensional space from a given electrode configuration, or determine an electrode configuration from a given position of the cathode pole 619. For example, the user can place the position of the cathode pole 619 using the cursor 601. The electrode configuration algorithm can then be used to compute an electrode configuration (e.g., current fractionalization across a plurality of selected active electrodes) that best places the cathode pole 619 in this position. The electrode configuration algorithm may thus calculate that electrode E4 should receive the largest share of cathodic current (52%*−I), while E2, E7, and E6 which are farther away from the cathode pole 619 receive lesser percentages, as shown in the stimulation parameters interface 604. By involving more than one electrode, cathode pole 619 is formed as a virtual pole not as the position of any of the physical electrodes. Again, the electrode configuration algorithm can also operate in reverse: from a given electrode configuration, the position of the cathode pole 619 can be determined. The electrode configuration algorithm is described further in U.S. Patent Application Publication 2019/0175915, which is incorporated herein by reference.

The GUI 600 can further include a visualization interface 606 that allows a user to view a stimulation field image 622 formed on a lead given the selected stimulation parameters and electrode configuration. The stimulation field image 622 is formed by field modelling in the CP 129. The visualization interface 606 may include tissue imaging information, such as imaging information of different brain tissue structures 624A, 624B and 624C in the context of DBS. Such tissue imaging information may come from a Magnetic Resonance Image (MRI) or Computed Tomography (CT) image of the patient, may come from a generic library of images, and may include user defined regions. The GUI 600 can overlay the lead image 621 and the stimulation field image 622 with the tissue imaging information in the visualization interface 606 so that the position of the stimulation field image 622 relative to the various tissue structures 624A-624C can be visualized. The various images shown in the visualization interface 606 (i.e., the lead image 621, the stimulation field image 622, and the tissue structures 624A-624C) can be three-dimensional in nature, and hence may be rendered to allow such three-dimensionality to be better appreciated by the user, such as by shading or coloring the images, etc. A view adjustment interface 607 may allow the user to use the cursor 601 to move or rotate the images. As illustrated in FIG. 6, a cross-section interface 608 allows the various images to be seen in a particular two-dimensional cross section, such as a cross section 609 taken perpendicularly to the lead image 621 and through the segmented electrodes E2, E3, and E4.

The GUI 600 can be particularly useful because it allows the electric field as reflected in stimulation field image 622 to be seen relative to surrounding tissue structures 624A-624C. This allows the user to adjust the stimulation parameters to recruit, or avoid recruiting, particular tissue structures. Assume for example that it is desirable for a given patient to stimulate tissue structure 624A, but to not stimulate tissue structures 624B or 624C where the stimulation may cause undesired side effects. The clinician can then use the GUI 600 to adjust stimulation (e.g., to adjust the stimulation parameters or the electrode configuration) to move the stimulation field (e.g., the cathode pole 619) to a proper position (L, θ). In the example shown, and as best seen in the cross-section interface 608, higher cathodic currents are provided at electrodes E4 (52%*–I) and E2 (18%*–I), because these electrodes are generally facing towards tissue structure 624A where stimulation is ideally applied. By contrast, electrode E3 carries no cathodic current because it generally faces towards tissue structure 624B where stimulation is ideally avoided. The result is a stimulation field that is more predominant in tissue structure 624A and less predominant in tissue structure 624B, as shown in the visualization interface 606.

Especially in a DBS application, it is important that correct stimulation parameters be determined for a given patient. Improper stimulation parameters may not yield effective relief of a patient's symptoms, or may cause unwanted side effects. To determine proper stimulation, a clinician may use the GUI 600 to try different combinations of stimulation parameters and electrode configurations. This may occur, during a DBS patient's surgery when the leads are being implanted, or during a post-surgery office visit after the patient has had a chance to heal and after the position of the leads stabilize in the patient. During an in-clinic testing and programming session, a clinician may use the GUI 600 that interacts with the feedback control logic 501 to generate one or more optimal base stimulation settings, as discussed above with reference to FIG. 5.

Figure 7:
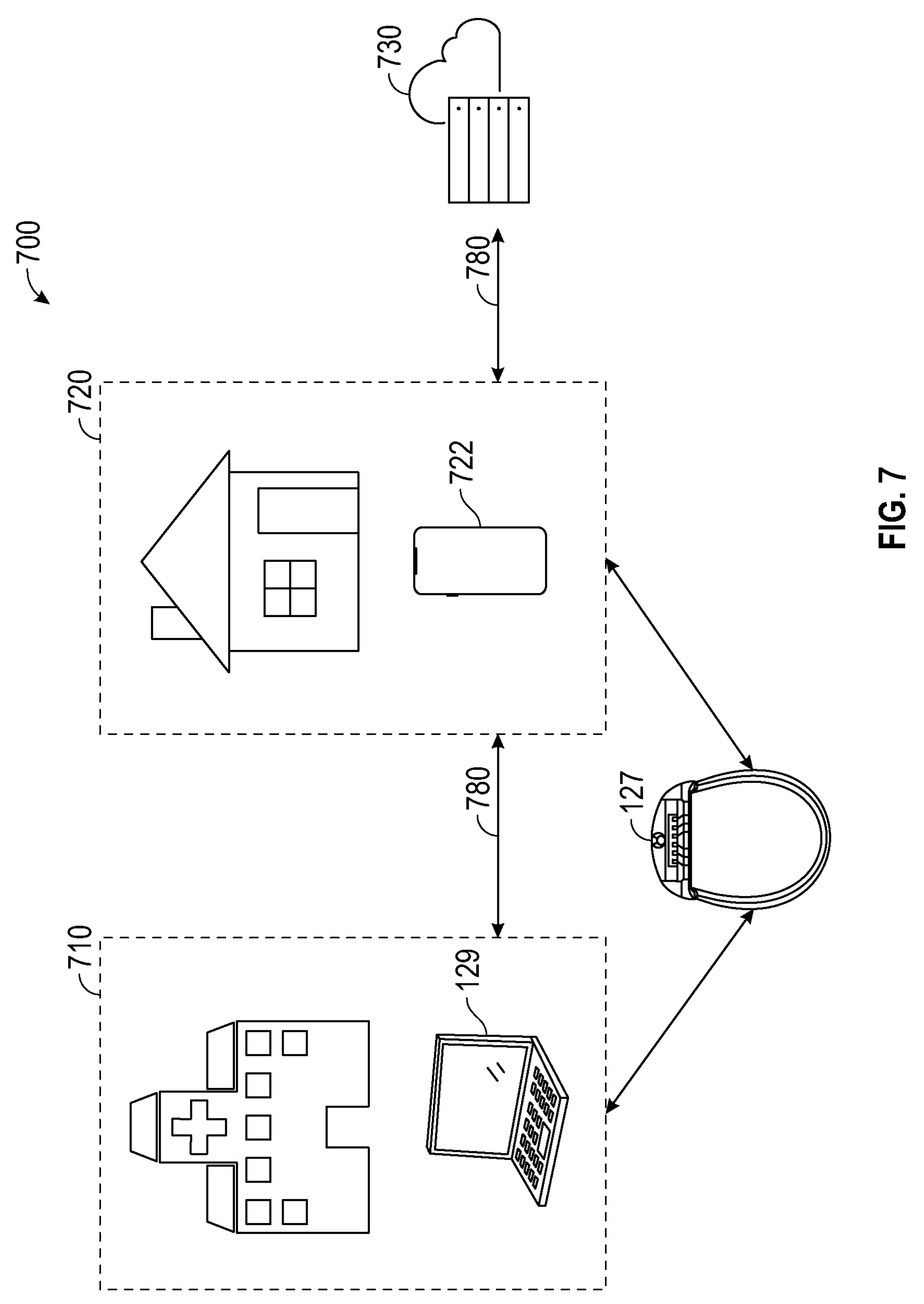
FIG. 7 illustrates an example of a cloud-based neuromodulation system that distributes stimulation programming between an in-clinic testing and programming session and one or more in-home therapy titration sessions.

As discussed above with reference to FIG. 5, in some examples, the feedback control logic 501 may be implemented in a CP 129 or in a RC 128. The CP 129 may be used in a clinical setting during IPG implantation or post-surgery office visit to generate, and store in the IPG, one or more optimal base stimulation settings (e.g., $BSS_1$-$BSS_8$ as discussed above) in an in-clinic testing and programming session. The base stimulation settings thus generated, even though deemed optimal at the time of programming (e.g., one or more clinical responses captured during the in-clinic testing and programming session satisfy a specific criterion), may nevertheless produce sub-optimal patient outcome such as due to changes in patient state (e.g., progression of an existing health condition or development of new health condition, or subsequent to treatment) monthly, weekly, daily, or even hourly after the in-clinic testing and programming session. Re-optimization at the clinic may not be practically or financially feasible for some patients. FIG. 7 illustrates an example of a cloud-based neuromodulation system 700 that can distribute the task of therapy optimization between an in-clinic testing and programming session in a clinical setting 710, and one or more in-home therapy titration sessions in the patient's home 720. The in-clinic testing and programming time and physician's effort can be reduced. In an example, the in-home therapy titration allows the patient to customize the stimulation setting to better address the patient's needs under the evolving medical conditions. The extended time also allowed for the in-home therapy titration allows for a better stimulation wash in effect, while also giving more timely, real-world feedback including a higher volume and a wide variety of clinical response variables including motor symptoms and non-motor symptoms) that are significant to the patient.

During the in-clinic testing and programming, a clinician may use the CP 129 to determine a search space of electrode configurations and parameter values, or a subspace thereof. During the in-home titration session, a patient or other authorized users may use a remotely controlled therapy titration device 722 to perform therapy optimization to search the search space (or the subspace) for an optimal stimulation setting for the patient. In an example, the therapy titration device 722 can be the RC 128. In another example, the therapy titration device 722 can be a smartphone, a tablet, or other mobile devices capable of executing a software application ("App") of therapy titration. The therapy titration device 722 may include an Application Programming Interface (API) that allows the user to request and retrieve from the IPG 127 one or more base stimulation programs 514 and the search space 512 stored in the memory 404, including the base stimulation program presently being used to provide DBS therapy. For example, if the IPG 127 is presently programmed with Program 4 in Table 1, the therapy titration device 722 may acquire clinical response information reported by the patient or automatically measured by a sensor in a wearable device operably in communication with the therapy titration device 722. The clinical response information indicates therapeutic effects and/or side effects of the base stimulation program. Due to changes in patient state, the acquired clinical responses may be different from the optimal or desired clinical responses observed during the course of in-clinic testing even though the same stimulation program (e.g., Program 4) is used to provide DBS therapy. The therapy titration device 722 may identify clinical effects (e.g., one or more of tremor, rigidity, or bradykinesia) that have worsened from what was recorded in the past during the in-clinic testing and programming session, and prioritize or boost the identified worsened clinical effects, such as by increasing the weights for the worsened clinical effects, and/or decreasing the weights for other clinical effects that have not worsened from the in-clinic testing and programming session. For example, if the presently acquired or measured clinical responses under Program 4 demonstrate that the tremor response has worsened from the past tremor response observed during in-clinic testing, then the therapy titration device 722 may increase the weight for the tremor response, such as from its previous weight 25% to a new weight 40%.

The therapy titration device 722 may additionally or alternatively decrease the weight for one or more other clinical effects, such as rigidity or bradykinesia. The therapy titration device 722 may implement the feedback control logic 501 as discussed above with reference to FIG. 5, and modify the present base stimulation program (e.g., Program 4) by modifying electrode configuration (e.g., selecting different electrodes) and/or adjusting values of one or more stimulation parameters within the stored search space 512, while evaluating a composite clinical response score defined with the new weights (e.g., Tremor response given a weight of 40%). In an example, the therapy titration device 722 may display on a GUI a graph of the search space such as those illustrated in FIGS. 8-9. The patient may search through the search space until a desired outcome is achieved, such as the clinical responses achieving a maximal or a desired amount of improvement in clinical effect. In some examples, therapy optimization (i.e., searching the search space for an optimal stimulation setting for the patient) can be carried out using the iterative optimization as discussed above with respect to the feedback control logic 501. In some examples, therapy optimization can be carried out with the assistance of cloud-based services, as to be discussed further below. The IPG 127 can then be programmed (e.g., by the DBS controller 505) with the modified stimulation program (e.g., Program 4'), replacing the existing base stimulation (e.g., Program 4). The modified stimulation program may be stored in the memory 404. In an example, the modified stimulation program may be stored in a new patient titrated program slot, which can be a dedicated memory space other than the space for storing the base stimulation programs. Alternatively, the base stimulation program in the memory may be overwritten by the modified stimulation program.

The therapy titration device 722 may include a communication module, such as a transceiver circuit, to establish data communication with the CP 129 and a remote computing device 730, such via a communication link 780. Examples of the communication link 780 may include Internet, LAN (Local Area Network), Wireless LAN (Wireless Local Area Network), WAN (Wide Area Network), PAN (Personal Area Network), or the like. In an example, the therapy titration device 722 is a smart phone operably connected to Internet via a cellular network, a WiFi network, or a physical connection such as Ethernet or modem, and transmit information to, and receive information from, the remote computing device 730. In an example, the remote computing device 730 can be a cloud-computing device (or "cloud"), which can be a cloud server or a plurality of networked devices. The cloud-computing device can include a cloud storage that can store data transmitted from networked devices such as the CP 129 or the therapy titration device 722. The cloud-computing device may include a suite of cloud-based services (e.g., software as a service, platform as a service, infrastructure as a service) allowing for secured, on-demand access by multiple clients (or "tenants").

The remote computing device 730 can evaluate the clinical response indicator, and determine a stimulation setting for the patient using cloud-based services. In an example, the cloud-based services include automatically downloading one or more candidate stimulation settings into the therapy titration device 722, and initiating the electrostimulation in accordance with the candidate stimulation settings. In some examples, the candidate stimulation settings can include candidate stimulation parameter (e.g., stimulation amplitude) values defined within the subspace of electrode configuration and parameter values that has previously been determined during the in-clinic testing and programming session, as to be discussed below with reference to FIGS. 8-9. The patient can operate the therapy titration device 722, such as via a user interface, to intervene the stimulation delivered in accordance with candidate stimulation settings (e.g., to skip a scheduled stimulation, or to terminate an on-going stimulation prematurely such as due to side effect experienced by the patient during stimulation), or to confirm or modify the selected stimulation setting. For example, the user may skip the automatic test, or terminate a test prematurely. In another example, the cloud-based services may include collecting and storing in a cloud storage clinical effect data in response to the electrostimulation delivered in accordance with candidate stimulation settings. The clinical effect data may include patient feedback on clinical effects of the electrostimulation via a user interface, and/or sensor signals via one or more sensors in response to the electrostimulation delivered in accordance with candidate stimulation settings. In some examples, the sensors may be configured to sense information about body motion (e.g., bradykinesia, tremor, or rigidity) such as in patients with Parkinson's disease. Examples of such sensors may include a motion sensor operably positioned on a leg or other body parts of the patient to sense the body motion, a sleep sensor attached to the patient or on a bed to sense body movement during sleep, or an imaging sensor (e.g., a camera or video recorder) for capturing images of body motion. In some examples, the sensors may be configured to sense information related to cognitive ability such as in patients with Alzheimer's disease. Examples of such sensors may include an audio sensor or an imaging sensor to record patient's verbal response or facial expressions in response to the electrostimulation delivered in accordance with candidate stimulation settings. In some examples, the audio and/or the imaging sensor may be automatically activated to record patient verbal response or facial expressions when the patient is making a phone call or a video call using the therapy titration device 722, during which the electrostimulation is delivered in accordance with the candidate stimulation settings. In some examples, the cloud-based services may include automatically scheduling the evaluation of the clinical response indicator in response to electrostimulation delivered in accordance with the candidate stimulation settings. The cloud-based services may include generate a report of clinical response to the stimulation settings being tested for the user (e.g., the patient), such as improvement in symptoms (e.g., tremor goes down from 30% to 10%).

Figure 8:
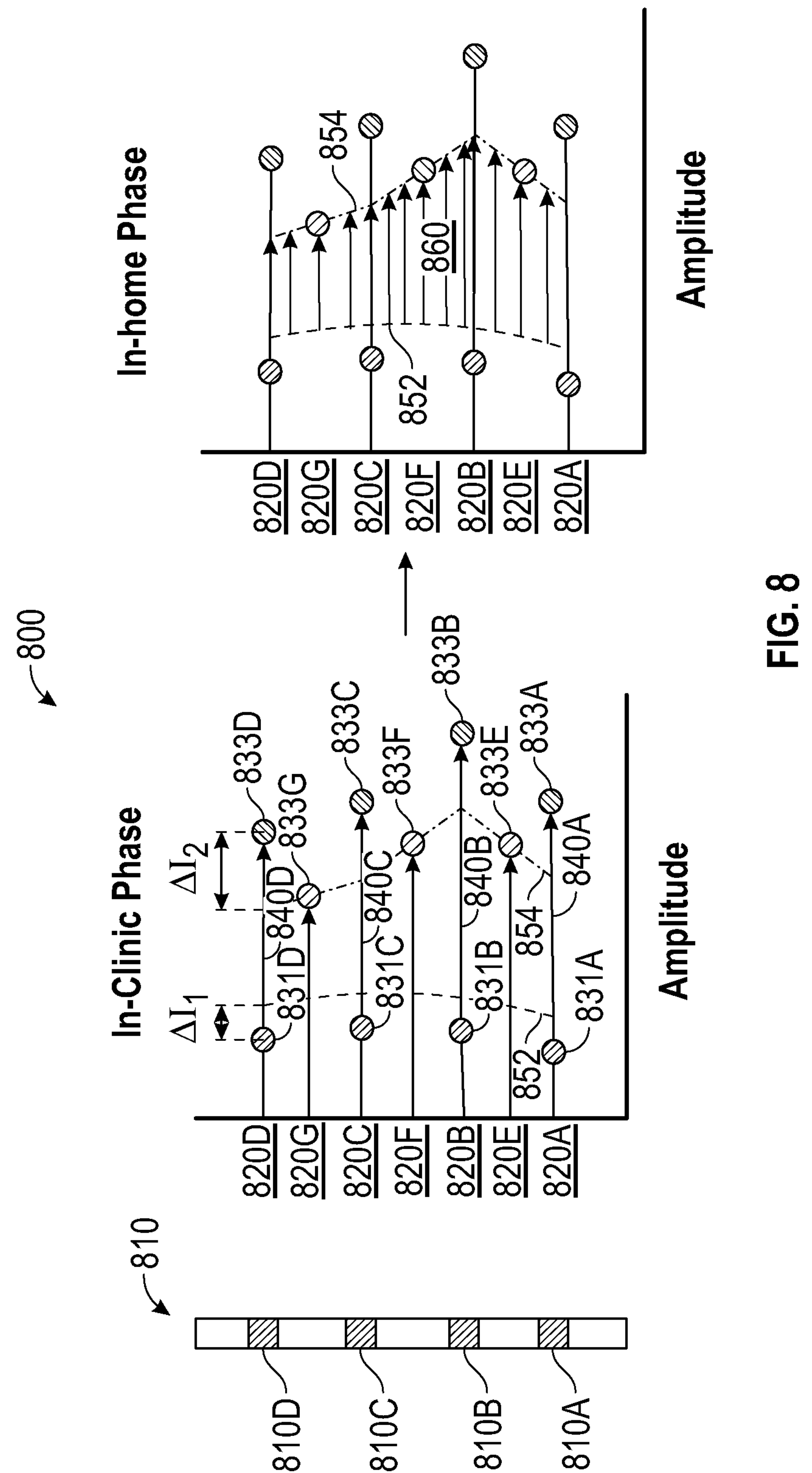
FIG. 8 illustrates a diagram of an electrode configuration and parameter search space, a subspace thereof, and a two-dimensional (2D) monopolar review of characteristic stimulation amplitudes corresponding to ring mode stimulation.
Figure 9:
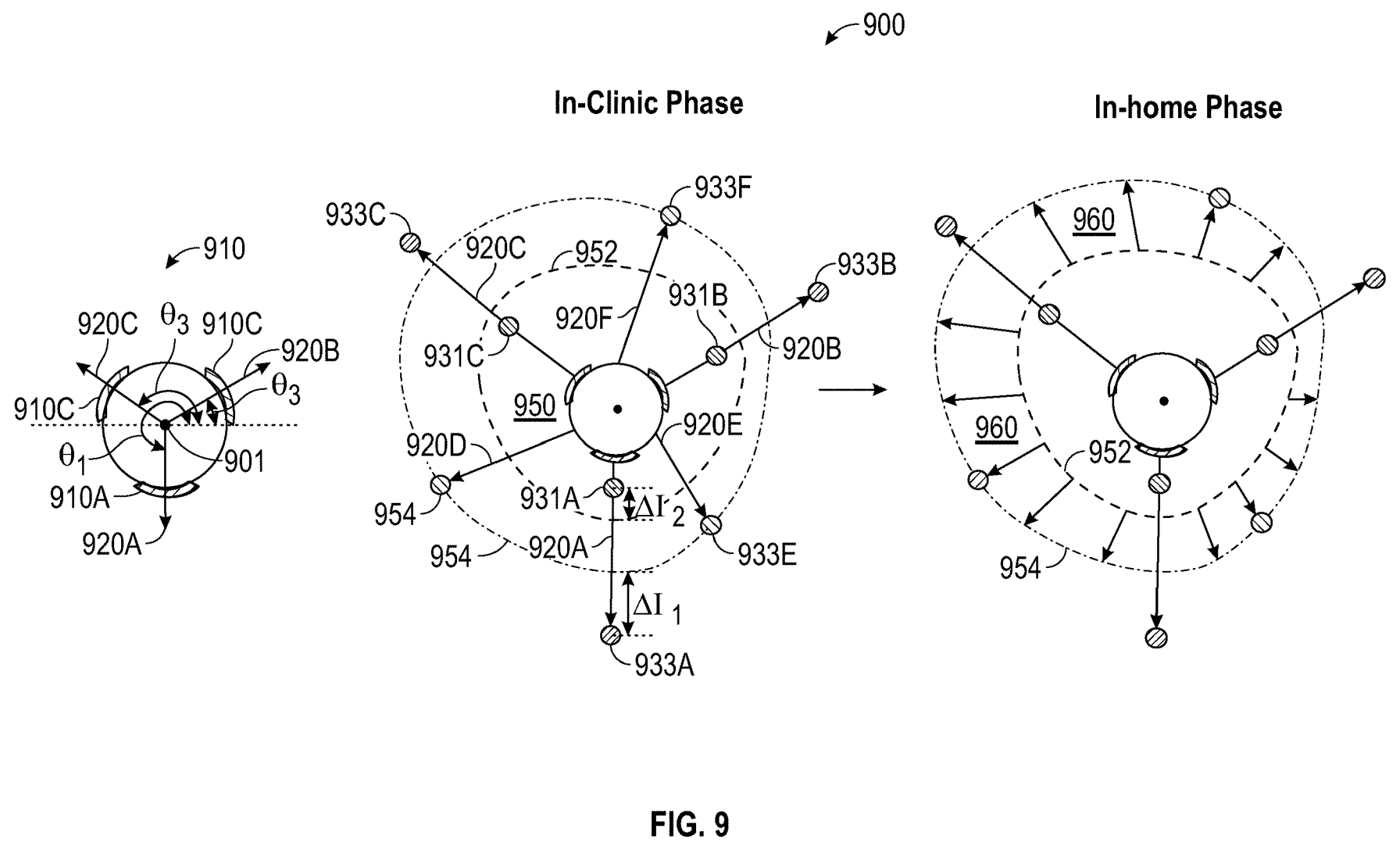

FIGS. 8-9 each illustrate, by way of example and not limitation, respective two-dimensional (2D) monopolar review diagrams of an electrode configuration and parameter search space (the "search space") and a subspace of the search space that can be provided to the patient for in-home therapy titration. In particular, FIG. 8 shows an electrode configuration and parameter search space, a subspace of the search space, and a monopolar review of characteristic stimulation amplitudes corresponding to ring mode stimulation. The ring mode stimulation can be delivered using a ring electrode, such as the electrode 216 on the non-directional lead 218. Alternatively, the ring mode stimulation can be delivered using multiple segmented electrodes around a circumference of a directional lead where stimulation current is spread substantially evenly to the segmented electrodes. FIG. 9 shows an electrode configuration and parameter search space, a subspace of the search space, and a monopolar review of characteristic stimulation amplitudes corresponding to directional mode stimulation, where separate and non-identical stimulation currents are applied to respective segmented electrodes, such as the electrodes 216 on the directional lead 219. The subspace can be determined during an in-clinic testing and programming session in the clinical setting 710 (as shown in FIG. 7). During an in-home therapy titration session, different candidate stimulation settings defined within the subspace can be automatically generated such as using the cloud services provided by the remote computing device 730. The candidate stimulation settings can be tested, and a stimulation setting can be identified for future electrostimulation therapy in the patient.

The search space defines electrode configurations and stimulation parameter values that may be used during the stimulation setting optimization to search for one or more optimal base stimulation settings. As discussed above, the search space may be identified, such as by the search space identifier 510, for a lead with known electrodes types and locations on the lead positioned at a target stimulation region such as a region in a brain hemisphere. The search space can be represented by a heatmap that depicts intensities of clinical responses measured or estimated over a range of electrode positions, such as longitudinal locations of the ring electrodes (as shown in FIG. 8) or angular locations of the segmented electrodes (as shown in FIG. 9) relative to the leads geometry and over a range of stimulation parameter values such as current amplitudes (represented by data points on a grayscale or colormap). The intensities of clinical responses may be represented by clinical response scores computed using, for example, a weighted combination of one or more clinical effects (e.g., bradykinesia, tremor, or rigidity). Clinical effects or clinical response scores may be evaluated for a plurality of electrodes at different locations, such as those electrodes involved in a first set of tested base stimulation settings (e.g., $BBS_1$-$BBS_4$ as discussed above with reference to FIG. 5. The clinical effects or clinical response scores may be evaluated in response to stimulation actually delivered with respective stimulation current amplitudes. Such actually tested clinical effects or the clinical response scores can be plotted as data points on the diagrams 800 and 900. Although the search space is defined by and graphically illustrated as a formatted monopolar review of characteristic stimulation amplitudes for one or more electrode configurations, it is to be understood, and within the scope of the present disclosure, that other stimulation parameters (other than stimulation amplitudes) may be similarly used to define the search space.

In addition to the actually tested clinical effects (in response to stimulation), clinical effects may be predicted for untested electrode configurations and untested stimulation parameter values, such as a second set of estimated base stimulation settings (e.g., $BBS_5$-$BBS_8$ as discussed above with reference to FIG. 5), without actually delivering electrostimulation. The prediction can be carried out using the machine learning engine 502 of the feedback control logic 501 as discussed above with reference to FIG. 5. Similar to the actually tested clinical effects, the predicted clinical effects or the clinical response scores may be plotted as data points on the diagrams 800 and 900.

The clinical effects (including both the tested and the predicted clinical effects as discussed above) may include both positive effects and negative effects. The diagram 800 can include a positive effect region 850 covering substantially data points representing actually tested and predicted positive effects. Similarly, the diagram 900 can include a positive effect region 950 covering substantially data points representing actually tested and predicted positive effects. The positive effect regions 850 and 950 each define a search space from which stimulation parameters and electrode configurations may be selected for an electrostimulation therapy without causing undesirable side effects. The positive effect regions 850 and 950 are also referred to as search spaces 850 and 950, respectively.

One or more characteristic stimulation amplitudes can be determined for each electrode configuration in the search space. An example of such electrode configuration is a monopolar configuration, which can include a single ring electrode or a single segmented electrode as cathode, and the device case 212 as anode. In some examples, by spreading cathodic current substantially evenly to a set of segmented electrodes around a circumference of the lead at a given longitudinal position, the segmented electrodes can be jointly configured as cathode, and the device case 212 as anode in a monopolar configuration. The characteristic stimulation amplitudes can be graphically displayed over the search space represented by a heatmap of the intensities of clinical responses measured or estimated over a range of electrode positions. FIG. 8-9 each depict respective monopolar review diagrams that can be displayed to a user (e.g., a physician). Such monopolar review diagrams can help the user better understand clinical effects of electrostimulations with a wide range of tested and untested electrode configurations and parameter values or value ranges, and guide the user to program electrostimulation therapy. As to be discussed further below, a subspace of the search space may be further be determined during the in-clinic testing and programming session. The subspace comprises a subset of the electrode locations and stimulation parameter values or value ranges at the subset of the electrode locations. The subspace defines a "safe search space" from which the patient may select electrode configuration and stimulation parameter value (e.g., stimulation amplitudes) during an in-home therapy titration session.

The characteristic stimulation amplitudes can be determined for one or more electrode configurations in the search space. The characteristic stimulation amplitude may be represented by stimulation parameters other than the current amplitude, such as voltage amplitude or stimulation energy applied to a specific electrode configuration. As discussed above with reference to FIG. 5, the characteristic stimulation amplitudes can be determined for electrode configurations directly tested within the search space, such as those configurations included in the first set of tested base stimulation settings (e.g., $BBS_1$-$BBS_4$ as discussed above with reference to FIG. 5). In addition to the actually tested clinical effects, clinical effects may be predicted for untested electrode configurations and untested stimulation parameter values, such as a second set of estimated base stimulation settings (e.g., $BBS_5$-$BBS_8$ as discussed above with reference to FIG. 5), without actually delivering electrostimulation. The prediction can be carried out using the machine learning engine 502 of the feedback control logic 501.

FIG. 8 illustrates a 2D monopolar review diagram 800 of at least a portion of the electrode configuration and parameter search space comprising a plurality of ring electrodes 810A-810D at respective ring mode stimulation positions (also referred to as vertical levels) 820A-820D on a non-directional lead 810 (an example of the non-direction lead 218). The diagram 800 may also represent an electrode configuration and parameter search space corresponding to segmented electrodes at a given longitudinal level of a directional lead (e.g., the directional lead 219) where current is spread approximately evenly to the segmented electrodes at that level, such that the segmented electrodes effectually deliver ring mode stimulation. The longitudinal positions of electrodes delivering ring mode stimulation (e.g., ring electrodes, or segmented electrodes jointly to deliver ring mode stimulation) are shown on the y-axis of the diagram 800. The x-axis represents a stimulation amplitude (e.g., current amplitude in milliamps (mA) up to an amplitude limit ($I_{max}$) set by a user) of a ring mode stimulation involving a ring electrode or a set of segmented electrodes at a given longitudinal position on the lead. For each ring mode stimulation position along the lead, multiple characteristic stimulation amplitudes, such as determined by the processor 402, can be graphically represented by markers linearly arranged along a direction with respect to the corresponding longitudinal position of the electrode(s) delivering the ring mode stimulation. In the illustrated example, for ring electrode 810A, two characteristic stimulation amplitudes are represented respectively by markers 831A and 833A along a direction 840A projecting from the ring mode stimulation position 820A of the ring electrode 810A. Similarly, markers 831B and 833B along a direction 840B represent characteristic stimulation amplitudes corresponding to the ring electrode 810B; markers 831C and 833C along a direction 840C represent characteristic stimulation amplitudes corresponding to the ring electrode 810C; and markers 831D and 833D along a direction 840D represent characteristic stimulation amplitudes corresponding to the ring electrode 810D.

The characteristic stimulation amplitudes each represent respective current amplitudes that, when applied to a specific electrode configuration, would result in respective clinical responses or clinical effects satisfying respective conditions. Such characteristic stimulation amplitudes can be searched or determined within the amplitude limit ($I_{max}$) that can be set by a user. In the illustrated example, the first characteristic stimulation amplitude $I_1$ (e.g., any one of 831A-831D) corresponds to a clinical response indicative of an initial improvement in patient symptom from a baseline. Depending on the conditions to be treatment by neuromodulation, such improvement can be assessed using physiological signals (e.g., heart rate, heart sounds, blood pressure), motor parameters (e.g., tremor, rigidity, bradykinesia, eye movements, facial movements, speech), non-motor parameters (e.g., sleep quality or alertness quality), or cognitive parameters indicative of patient cognitive abilities. In an example, $I_1$ can be determined as the current amplitude corresponding to an initial improvement in symptom from baseline by a given amount. In another example, $I_1$ corresponds to first time the clinical response score reaches a specific level relative to (such as X % of) the current best clinical response score, where X % can be approximately 10-80% in an example.

The second characteristic stimulation amplitude $I_2$ (e.g., any one of 833A-833D) corresponds to a side effect being detected or reported by the patient, or a loss of improvement of patient symptom from the baseline. In an example, $I_2$ can be determined as the current amplitude corresponding to the side effect being immediately below, or reaching a given amount (e.g., X %) from, an expected side effect. In an example, $I_2$ can be determined as the current amplitude corresponding to the therapeutic effect returning to pre-treatment baseline, within a given amount of the baseline, or outside given amount of the best clinical response score. If no side effect or loss of symptom improvement is reported when the stimulation current reaches the limit $I_{max}$, $I_2$ can be equivalent to $I_{max}$. In some examples, the characteristic stimulation amplitude (e.g., $I_1$ or $I_2$) can be a minimum stimulation amplitude within a specific amplitude range that produces respective clinical response indicators or clinical effects satisfying respective conditions.

In some examples, characteristic stimulation amplitudes may be determined for an intermediate ring mode stimulation position other than the positions of the physical electrodes on the lead (e.g., ring mode stimulation positions 820A-820D corresponding to the ring electrodes 810A-810D). As illustrated in FIG. 8, intermediate ring mode stimulation positions 820E, 820F, and 820G are each located between two ring mode stimulation positions among 820A-820D. A characteristic stimulation amplitude (e.g., $I_1$ or $I_2$) can be determined for an intermediate ring mode stimulation position based on the clinical response scores (including both the tested clinical response scores and the estimated clinical response scores) in the search space using similar methods for generating the characteristic stimulation amplitude for the ring mode stimulation positions 820A-820D as discussed above. FIG. 8 shows by way of example stimulation current $I_2$ markers 833E, 833F, and 833G for intermediate ring mode stimulation positions 820E, 820F, and 820G, respectively.

A therapeutic window can be determined for a stimulation position using the characteristic stimulation amplitudes for that stimulation position. The therapeutic window represents a range of stimulation amplitudes that can be programmed to the corresponding electrode without introducing substantial side effects. The therapeutic window can be determined for any ring mode stimulation position, including the stimulation positions 820A-820D and the intermediate stimulation positions 820E-820G, and graphically displayed on the diagram 800. In an example, for any ring mode stimulation position, the therapeutic window can be defined between the first characteristic stimulation amplitude $I_1$ and the second characteristic stimulation amplitude $I_2$. In another example, the therapeutic window can be defined as a portion within the range between $I_1$ and $I_2$, such as between $I_1+\Delta I_1$ and $I_2-\Delta I_2$, where $\Delta I_1$ is an effectiveness margin for $I_1$, and $\Delta I_2$ is a safety margin for $I_2$ at the corresponding ring mode stimulation position. The margins $\Delta I_1$ or $\Delta I_2$ can be determined or adjusted by a clinician during an in-clinic testing and programming session. The therapeutic windows for respective ring mode stimulation positions (e.g., 820A-820G) collectively form a subspace 860 within the search space 850. As shown in FIG. 8, the subspace 860 defines a stimulation parameter value zone (e.g., stimulation amplitude zone) graphically represented by a parameter value plane parallel to the length of the lead. When the therapeutic windows for respective electrode positions are determined using the margins $\Delta I_1$ and $\Delta I_2$, the subspace 860 is defined between (i) a first boundary 852 representing $I_1+\Delta I_1$ values across the electrode positions 820A-820G and (ii) a second boundary 854 representing $I_2-\Delta I_2$ values across the electrode positions 820A-820G.

The subspace 860 (including the first and the second boundaries 852 and 854) can be determined during the in-clinic testing and programming session in a clinical setting 710 (as shown in FIG. 7) using the CP 129. The determined subspace can be provided to a user (e.g., patient) such as in the patient's home 720, where different candidate stimulation settings within the subspace 860 can be tested in an in-home therapy titration session using the therapy titration device 722, and an optimal stimulation setting can be identified for future electrostimulation therapy in the patient. The in-home therapy titration can be performed in an on-demand (i.e., initiated by a user or the patient), periodically, or triggered by a medical event such as worsening of symptoms. In an example, the in-home therapy titration can be done in multiple sessions over a time period, such as days or weeks. As described above with reference to FIG. 7, the therapy titration device 722 can be communicatively coupled to the remote computing device 730, such as a cloud-computing device that can evaluate the clinical response indicator or to select the stimulation setting using cloud-based services. The cloud-based services may include automatically downloading one or more the candidate stimulation settings into the therapy titration device and initiating the electrostimulation in accordance with the candidate stimulation settings. By way of example and not limitation, such candidate stimulation settings can include different candidate stimulation amplitudes applied to different ring mode stimulation positions (e.g., 820A-820G) within the subspace 860 defined between the first boundary 852 and the second boundary 854. In an example, the in-home testing and therapy titration can be done sequentially, such as by first testing stimulation at a ring mode stimulation position (i.e., vertical level) such as 820A, followed by testing stimulations at various angular positions at that vertical level. In some examples, the base stimulation settings (e.g., $BBS_1$-$BBS_4$ as discussed above with reference to FIG. 5) determined during the in-clinic testing and programming session may be used as a starting point during the in-home testing and therapy titration. Candidate stimulation settings to be tested during the in-home therapy titration session can be modifications of the base stimulation settings, such as modified stimulation amplitude or modified stimulation positions. Clinical effect data collected during the electrostimulation delivered in accordance with candidate stimulation settings can be stored in a cloud storage. Examples of the clinical effect data include a user feedback on clinical effects of the electrostimulation via a user interface, or sensor signals via one or more sensors in response to the electrostimulation delivered in accordance with candidate stimulation settings. The user feedback may be provided by the patient. Additionally or alternatively, the user feedback may include observations of the patient's clinical effects provided by a secondary party (e.g., a caregiver of the patient) whom the patient has consented to supply such information.

FIG. 9 illustrates a 2D monopolar review diagram 900 of at least a portion of an electrode configuration and parameter search space comprising a plurality of segmented electrodes 910A-910C at different angular positions 920A-920C around a circumference of a directional lead 910 at a specific vertical location, where separate and non-identical stimulation currents are applied to respective segmented electrodes to deliver directional mode stimulation. For each segmented electrode, multiple characteristic stimulation amplitudes, such as determined by the processor 402, can be graphically represented by markers linearly arranged along a direction 9 at an angle $\theta$ (relative to a reference direction) consistent with the angular position of the corresponding segmented electrode. The radius of the circular shape in diagram 900 represents a stimulation amplitude (e.g., current amplitude I in mA), up to an amplitude limit ($I_{max}$) that can be set by a user, applied to the monopolar configuration involving a segmented electrode. In the illustrated example, for segmented electrode 910A, two characteristic stimulation amplitudes can be represented respectively by markers 931A and 933A along a direction projecting from the lead center position 901 at an angle $\theta_1$ based on the angular position 920A of the segmented electrode 910A. Similarly, for segmented electrode 910B, characteristic stimulation amplitudes are represented by markers 931B and 933B along a direction projecting from the lead center position 901 at an angle $\theta_2$ based on the angular position 820B of the segmented electrode 810B. For segmented electrode 910C, characteristic stimulation amplitudes are represented by markers 931C and 933C along a direction projecting from the lead center position 901 at an angle $\theta_3$ based on the angular position 920C of the segmented electrode 910C. Similar to the characteristic stimulation amplitudes $I_1$ and $I_2$ for the ring mode stimulation positions as shown in FIG. 8, here in FIG. 9 the characteristic stimulation amplitudes can be searched or determined within the amplitude limit ($I_{max}$), represented by the radius of the circular shape, that can be set by a user. The characteristic stimulation amplitudes can include a first amplitude $I_1$ (any one of 931A-931C) corresponding to a clinical response indicative of an initial improvement in patient symptom from a baseline, and a second amplitude $I_2$ (any one of 933A-933C) corresponding to a side effect being detected or reported by the patient, or a loss of improvement of patient symptom from the baseline. In some examples, for each of the segmented electrodes 910A-910C, a therapeutic window can be defined between two characteristic stimulation amplitudes for that electrode, such as between the first amplitude $I_1$ and the second amplitude $I_2$. In some examples, characteristic stimulation amplitudes (e.g., $I_1$ and $I_2$) can be determined for intermediate angular positions different than the angular positions 920A-920C of the respective segmented electrodes 910A-910C on the lead, such as stimulation current $I_2$ markers 933D, 933E, and 933F for respective intermediate angular positions 920D, 920E, and 920F.

A therapeutic window can be determined for each of the angular positions, including the angular positions 920A-920C of the respective segmented electrodes 910A-910C and the intermediate angular positions 920D-920F. Similar to the description above with respect to FIG. 8, for an angular position, a therapeutic window can be defined between $I_1+\Delta I_1$ and $I_2-\Delta I_2$, where $\Delta I_1$ is an effectiveness margin for $I_1$, and $\Delta I_2$ is a safety margin for $I_2$. The margins $\Delta I_1$ or $\Delta I_2$ can be determined or adjusted by a clinician during an in-clinic testing and programming session. A subspace 960 within the search space 950 can be formed using the therapeutic windows for the angular positions. The subspace 960 defines a stimulation parameter value zone (e.g., stimulation amplitude zone) graphically represented by a parameter value plane perpendicular to the length of the lead. As illustrated in FIG. 9, the subspace 960 can be defined between (i) a first boundary 952 representing $I_1+\Delta I_1$ values across the angular positions 920A-920F and (ii) a second boundary 954 representing $I_2-\Delta I_2$ values across the angular positions 920A-920F.

The subspace 960 (including the first and the second boundaries 952 and 954) can be determined during an in-clinic testing and programming session in a clinical setting 710. The determined subspace can be provided to a user (e.g., the patient or an authorized personnel such as a caregiver of the patient) such as in the patient's home 720, where different candidate stimulation settings within the subspace 960 can be tested in one or more in-home therapy titration sessions, and an optimal stimulation setting can be identified for future electrostimulation therapy in the patient. The in-home therapy titration can be performed in an on-demand (i.e., initiated by a user or the patient), periodically, or triggered by a medical event such as worsening of symptoms. In an example, the in-home therapy titration can be done in multiple sessions over a time period, such as days or weeks. As similarly described with respect to FIG. 8, a cloud-computing device can evaluate the clinical response indicator or to select the stimulation setting using cloud-based services. The cloud-based services may include automatically downloading one or more the candidate stimulation settings into the therapy titration device and initiating the electrostimulation in accordance with candidate stimulation settings. By way of example and not limitation, such candidate stimulation settings can include candidate stimulation amplitudes at different angular positions (e.g., 920A-920F) within the subspace 960, such as between the first boundary 952 and the second boundary 954. Clinical effect data collected during the electrostimulation in accordance with candidate stimulation settings can be stored in a cloud storage.

The characteristic stimulation amplitudes for each ring mode stimulation position (ring electrode or segmented electrode) as shown in FIGS. 8-9 represents stimulation amplitudes (e.g., current I) when other stimulation parameters, such as frequency (F) and pulse width (PW) as shown in FIG. 6, are fixed at receptive values (e.g., frequency of 130 Hz and PW of 60 μs). When the frequency (F) or pulse width (PW) are reprogrammed to different values, a different monopolar review diagram (similar to that shown in FIG. 8 or 9) can be generated, where the markers representing one or more of the characteristic stimulation amplitudes for a ring electrode or a segmented electrode can be repositioned along the line projecting from that ring electrode or segmented electrode.

In some examples, the 2D monopolar review diagram 800 for ring electrodes at different longitudinal levels of a lead (or for segmented electrodes of a given longitudinal level that are programmed to deliver ring mode stimulation may be combined with the 2D monopolar review diagram 900 for segmented electrodes at a common longitudinal level that are programmed to deliver directional mode stimulation. In an example, the diagrams 800 and 900 may be stacked on top of each other. The combined monopolar review may include characteristic stimulation amplitudes (e.g., $I_1$ and $I_2$ as described above in reference to FIG. 8) for each ring electrode (or each set of segmented electrodes delivering ring mode stimulation), and characteristic stimulation amplitudes (e.g., $I_1$ and $I_2$ as described above in reference to FIG. 9) for each segmented electrode at a common longitudinal level of the lead. As the subspace 860 can be represented by a two-dimensional parameter value plane parallel to the length of the lead, and the subspace 960 can be represented by a two-dimensional parameter value plane perpendicular to the length of the lead, by stacking diagrams 800 and 900, a three-dimensional parameter value space (spanned by the subspace 860 and the subspace 960) can be formed and presented to the user. The combined monopolar review may be especially helpful to better understand clinical effects of electrostimulation using electrode configurations involving ring electrodes and segmented electrodes on a lead (e.g., the directional lead 219).

The diagrams 800 or 900 may be displayed to a user, such as on the GUI 600 of the CP 129, where a user (e.g., a clinician or the patient) may select active electrodes or adjust stimulation parameter values within the subspace 860 or 960. For example, the user may only be allowed to select stimulation current amplitude for an electrode at a particular location to be within a specific amplitude range. In some examples, the diagrams 800 or 900 may be displayed on a user interface of the RC 128, such as a mobile device (e.g., a smartphone or a tablet) operable by the patient for in-home titration of an base stimulation program.

In some examples, the subspaces as described above and shown in FIGS. 8 and 9 can be used in the cloud-based neuromodulation system 700 to optimize deep brain stimulation (DBS) separately for left and right hemisphere of the brain. The IPG 127 may be configured to provide DBS to a brain target via one or more leads each configured to be positioned in a left or right hemisphere of the brain. The CP 129 can identify a first subspace comprising electrode locations and the stimulation parameter values or value ranges for DBS of the left hemisphere of the brain, and to separately identify a second subspace comprising electrode locations and the stimulation parameter values or value ranges for DBS of the right hemisphere of the brain. The therapy titration device 722 can select a first stimulation setting from the first subspace for the DBS of the left hemisphere, and a second stimulation setting from the second subspace for the DBS of the right hemisphere.

Figure 10:
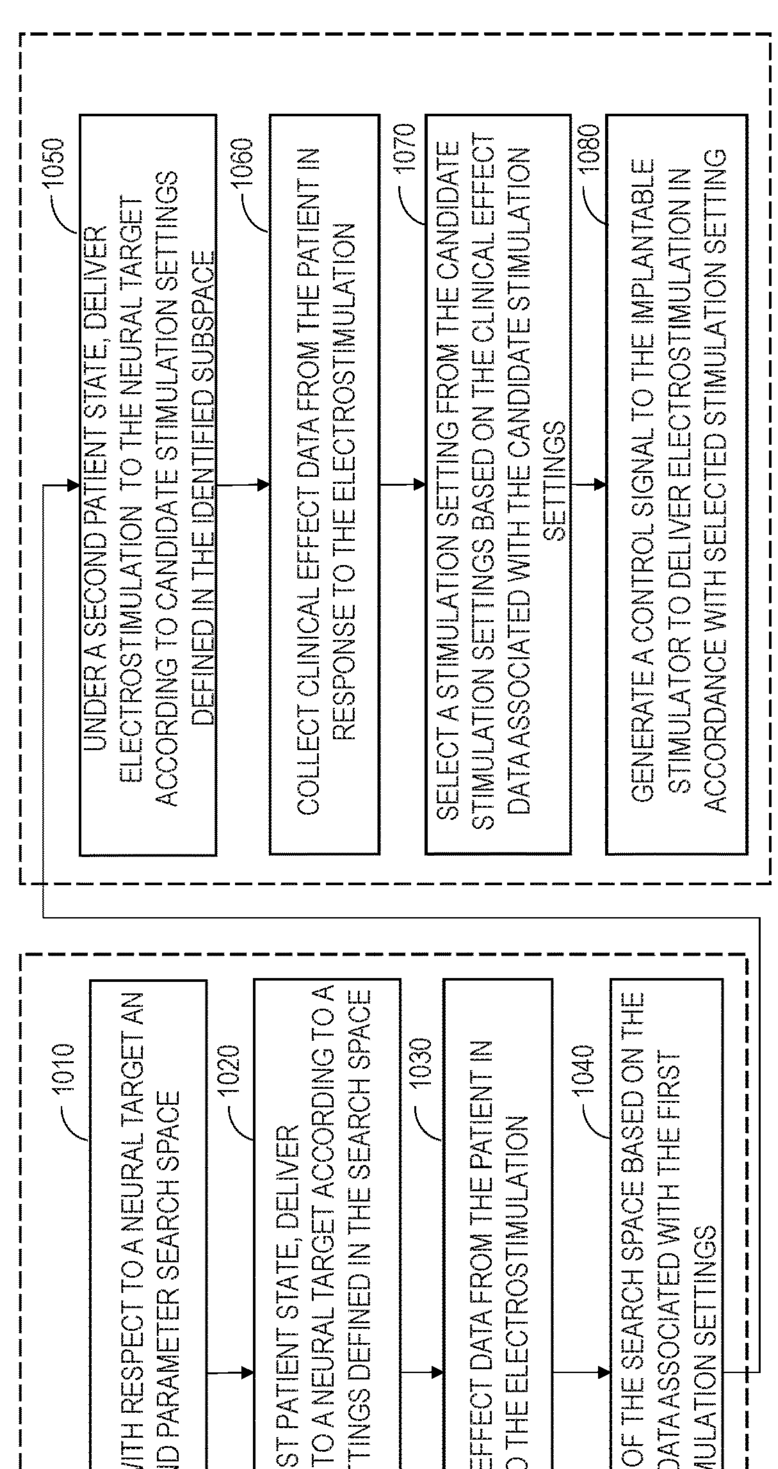
FIG. 10 is a flow chart illustrating an example method of in-home titration of electrostimulation using cloud-based services.

FIG. 10 is a flow chart illustrating, by way of example and not limitation, a method 1000 for optimizing neurostimulation, such as deep brain stimulation, at a patient home using cloud-based services. The method 1000 may be carried out using a medical system such as the electrical stimulation system 100 in FIG. 1, or the electrical stimulation system 412 in FIG. 4. The electrostimulation may be generated by an implantable stimulator such as the IPG 127 or the IPG 210, and delivered to the neural target via a lead comprising a plurality of electrodes, such as the non-directional lead 218 or the directional lead 219. Portions of the method 1000 may be implemented in the computing device 400 as shown in FIG. 4, cloud-based neuromodulation system 700 as shown in FIG. 7.

The method 1000 includes steps 1010-1040 for generating and storing in a memory a search space of electrode configurations and parameter values (also referred to as a "search space"), a subspace thereof, and one or more base stimulation settings, and steps 1050-1080 for cloud-based therapy optimization. Steps 1010-1040 can be performed in an in-clinic testing and programming session under a first patient condition, such as using the CP 129. Steps 1050-1080 can be performed in one or more in-home therapy titration sessions under a different second patient condition, such as using the therapy titration device 722. At 1010, a search space for the lead with respect to the neural target can be identified, such as using the search space identifier 510. The search space can include a subset of the electrodes on the lead for delivering stimulation and stimulation parameter values or value ranges associated with the subset of electrodes. Identification of the search space can be based on spatial information of the lead, such as lead positions with respect to neural targets, which can be obtained from imaging data of the lead and patient anatomy. Additionally or alternatively, identification of the search space can be based on physiological information such as physiological signals sensed locally at electrode contacts. Certain limitations or constraints may be imposed on the electrode configurations and parameter values (e.g., current amplitude, frequency, or pulse width). In some examples, the search space may be graphically presented as a heatmap depicting intensities of clinical responses to stimulations delivered over a range of electrode positions and over a range of stimulation parameter values.

At 1020, under a first patient state (such as a state when the patient receives the IPG 127 and stimulation leads 218 or 219 during an implant procedure), electrostimulation may be delivered to a neural target (e.g., brain tissue target) using an implantable stimulator such as the IPG 127 and a stimulation lead in accordance with first stimulation settings defined within the search space. At 1030, clinical effect data can be collected from the patient in response to the electrostimulation delivered in accordance with the first stimulation settings, and a clinical response indicator can be evaluated using the collected clinical effect data.

The evaluation of the clinical response indicator can be performed using a programming device such as the CP 129 during the in-clinic testing and programming session. Clinical responses may be evaluated for a plurality of electrodes at different locations and injected with respective stimulation current amplitudes. The clinical response may include therapeutic benefits and/or side effects on the patient. In an example, the clinical responses may be based on patient or clinician observations. For example, motor symptoms such as bradykinesia (slowness of movement), rigidity, tremor, among other symptoms or side effects, can be scored by the patient or by the clinician upon overserving or questioning the patient. In some examples, the clinical responses can be objective in nature, such as measurements automatically or semi-automatically taken by a sensor, such as a wearable sensor associated with a mobile device. The clinical responses may be converted to a clinical response score. In an example, a clinical score may be computed based on intensity, frequency, or duration of one or more of tremor, rigidity, or bradykinesia responses.

In some examples, one or more base stimulation settings may be determined based on the evaluation of the clinical response indicator. A base stimulation setting can correspond to a clinical response indicator satisfying a specific condition, such as the clinical response score falling within a specified range. A base stimulation setting, which includes an optimal electrode configuration and an optimal stimulation parameter value, can be determined using the feedback loop stimulation parameter control system 500, in which the electrode configuration or values of one or more stimulation parameters can be continuously or iteratively adjusted and the clinical response evaluated, until an optimal, desired, or acceptable outcome is reached, such as maximizing therapeutic efficacy while minimizing unwanted side effects, or until a specific stop condition is reached such as number of iterations, time spent in programming session, or the like. Each base stimulation setting can be associated with a clinical response indicator. A stimulation setting in association with the clinical response indicator (e.g., a formula for computing the clinical response score) is referred to as a stimulation program. Depending on how the clinical response score is computed, one or more optimal base stimulation settings may be determined. As described above with reference to FIG. 5, base stimulation settings may include those base stimulation settings associated with the clinical response scores computed based on a single response effect (e.g., bradykinesia, tremor, or rigidity), or stimulation settings associated with clinical response scores computed using a weighted combination of two or more clinical effects, such as a %*bradykinesia+b %*tremor+c %*rigidity. In some examples, one or more base stimulation settings may be determined using predicted clinical responses for untested stimulation parameter values or untested electrode configurations without actually delivering electrostimulation and evaluating the resultant clinical responses. Such untested stimulation parameter values and untested electrode configurations are referred to as second stimulation settings to distinguish from the first stimulation settings that have been tested (i.e., with stimulation delivered). The prediction may be carried out using a trained prediction model, such as the machine learning engine 502 of the feedback control logic 501 in FIG. 5. The stimulation settings generated based on the predicted clinical responses are also referred to as estimated base stimulation settings, such as base stimulation settings $BSS_5$-$BSS_8$.

At 1040, a subspace of the search space can be identified based at least in part on the clinical response indicator associated with the first stimulation settings. In some examples, the subspace can be identified further based on the clinical response indicator associated with the second stimulation settings. The subspace comprises stimulation positions and a stimulation parameter value zone defined between first and second characteristic parameter values for each of the electrode locations. The first and second characteristic parameter values each correspond to respective clinical response indicators satisfying respective conditions. In an example, the first characteristic parameter value is a first current amplitude $I_1$ corresponding to an initial improvement in symptom from baseline by a given amount, the second characteristic parameter value is a second current amplitude $I_2$ corresponding to a side effect being detected or reported by the patient.

As described above with reference to FIGS. 8 and 9, a therapeutic window can be determined for a stimulation position (such as one of the ring mode stimulation positions 820A-820G, or one of the angular stimulation positions 920A-920F) using the characteristic stimulation amplitudes (e.g., $I_1$ and $I_2$) for that stimulation position. The therapeutic window represents a range of stimulation amplitudes that can be programmed to the corresponding electrode without introducing substantial side effects. In an example, the therapeutic window can be defined between the first characteristic stimulation amplitude $I_1$ and the second characteristic stimulation amplitude $I_2$. In another example, the therapeutic window can be defined as a portion within the range between $I_1$ and $I_2$, such as between $I_1+\Delta I_1$ and $I_2-\Delta I_2$, where $\Delta I_1$ is an effectiveness margin for $I_1$, and $\Delta I_2$ is a safety margin for $I_2$ at the corresponding ring mode stimulation position. The margins $\Delta I_1$ or $\Delta I_2$ can be determined or adjusted by a clinician during an in-clinic testing and programming session.

The subspace identified from step 1040, optionally along with the search space identified from step 1010 as well as one or more base stimulation settings (and the associated clinical response indicators) can be stored in a memory internal to the IPG or a cloud storage in the remote computing device 730. Upon request, the subspace and one or more base stimulation settings may be retrieved and used in an in-home therapy titration session. The in-home therapy titration can be performed in an on-demand (i.e., initiated by a user or the patient), periodically, or triggered by a medical event such as worsening of symptoms. In an example, the in-home therapy titration can be done in multiple sessions over a time period, such as days or weeks. At 1050, under a second patient state different from the first patient state (such as a post-implant state when the patient is performing in-home therapy optimization), electrostimulation may be delivered in using an implantable stimulator such as the IPG 127 and the implanted leads in accordance with candidate stimulation settings defined in the subspace previously identified at step 1040. As described above with reference to FIGS. 7-9, the patient may use the therapy titration device 722 to download one or more candidate stimulation settings from the remote computing device 730, which can be a cloud-computing device. Cloud-based services may be used to initiate electrostimulation in accordance with the candidate stimulation settings. By way of example and not limitation, such candidate stimulation settings can include different candidate stimulation amplitudes applied to different stimulation positions (e.g., ring mode stimulation positions 820A-820G or angular stimulation positions 920A-920F) within the identified subspace. In an example, the in-home testing and therapy titration can be done sequentially, such as by first testing stimulation at a ring mode stimulation position (i.e., vertical level), followed by testing stimulations at various angular positions at that vertical level. In some examples, the base stimulation settings (e.g., $BBS_1$-$BBS_4$ as discussed above with reference to FIG. 5) determined during the in-clinic testing and programming session may be used as a starting point during the in-home testing and therapy titration. Candidate stimulation settings to be tested during the in-home therapy titration session can be modifications of the base stimulation settings, such as modified stimulation amplitude or modified stimulation positions.

At 1060, clinical effect data can be collected from the patient in response to the electrostimulation delivered in accordance with the candidate stimulation settings, and a clinical response indicator can be evaluated using the collected clinical effect data. Examples of the clinical effect data include a user feedback on clinical effects of the electrostimulation via a user interface, or sensor signals via one or more sensors in response to the electrostimulation delivered in accordance with candidate stimulation settings. Due to changes in patient state, the clinical response (or some clinical effects) may be different from the optimal or desired clinical responses observed during the course of the in-clinic testing and programming session. During the in-home therapy titration, the patient can user the therapy titration device 722 to intervene the stimulation delivered in accordance with candidate stimulation settings (e.g., to skip a scheduled stimulation, or to terminate an on-going stimulation prematurely such as due to side effect experienced by the patient during stimulation), or to confirm or modify the selected stimulation setting. For example, the user may skip the automatic test, or terminate a test prematurely.

At 1070, an optimal stimulation setting may be selected from the candidate stimulation settings based at least in part on the clinical response indicator associated with the candidate stimulation settings. In an example, the optimal stimulation setting can be determined when the corresponding clinical score satisfies a condition, such as exceeding a threshold. In an example, the optimal stimulation setting may be determined by modifying a based stimulation setting within the identified subspace. In an example, for a base stimulation setting, the clinical response indicator presently evaluated under the second patient state can be compared with the clinical response indicator previously evaluated under the first patient state. Based on the comparison, one or more clinical effects (e.g., tremor, rigidity, or bradykinesia) that have worsened from the first patient state to the second patient state can be identified. The clinical response indicator may be modified such by increasing the weights for the worsened clinical effects, or additionally or alternatively decreasing the weights for other clinical effects that have not worsened. The base stimulation setting may be modified such as by iteratively adjusting the optimal electrode configuration or the optimal stimulation parameter value within the identified subspace, until the modified clinical response indicator satisfies a specific condition under the second patient state. The modified base stimulation setting, in association with the modified clinical response indicator, can then be recommended as the optimal stimulation setting for the patient. At 1070, a control signal can be generated to control the implantable stimulator to deliver electrostimulation in accordance with the selected optimal stimulation setting.

Figure 11:
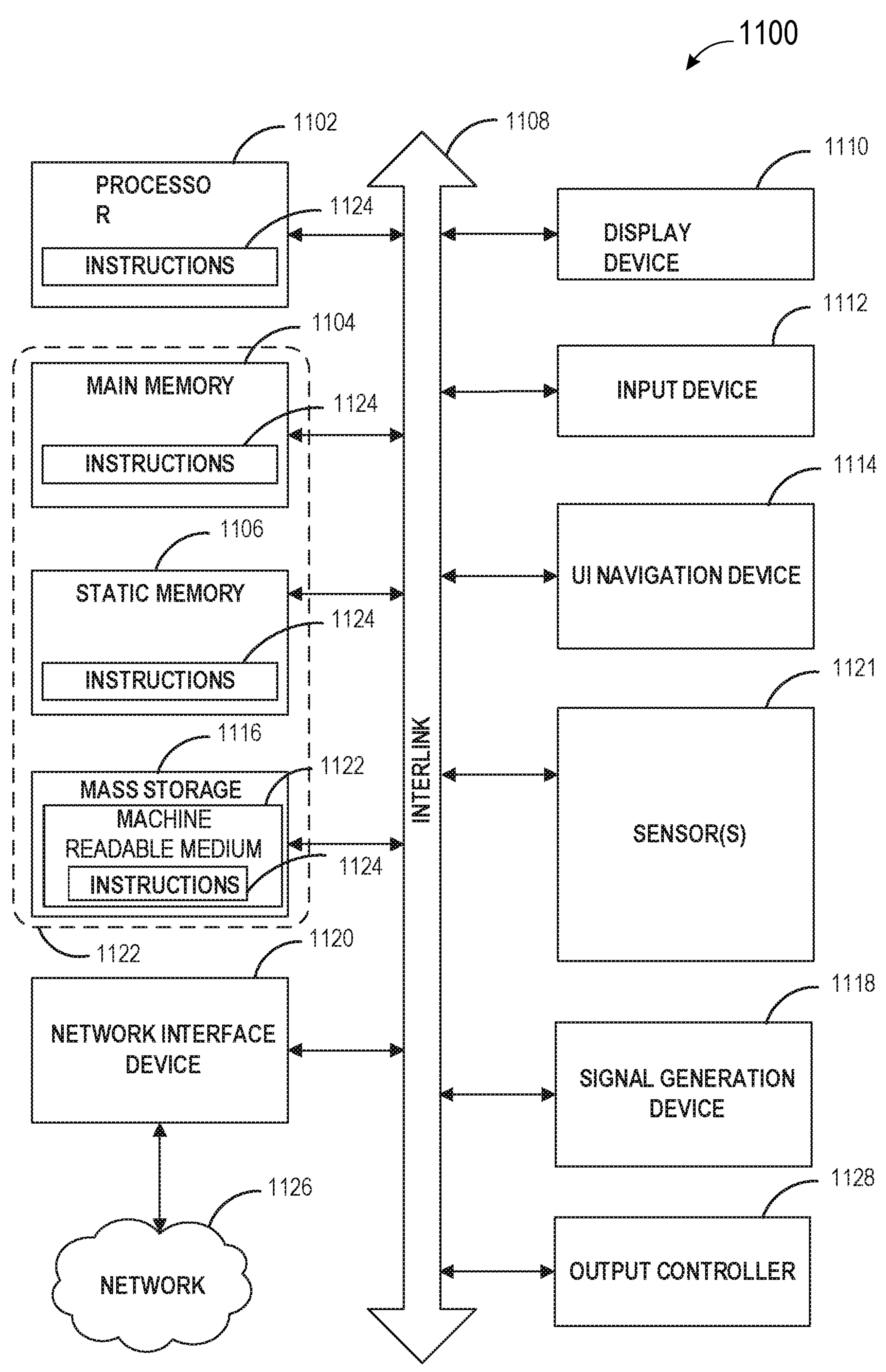
FIG. 11 illustrates generally a block diagram of an example machine upon which any one or more of the techniques (e.g., methodologies) discussed herein may perform.

FIG. 11 illustrates generally a block diagram of an example machine 1100 upon which any one or more of the techniques (e.g., methodologies) discussed herein may perform. Portions of this description may apply to the computing framework of various portions of the neuromodulation device or the external programming device.

In alternative examples, the machine 1100 may operate as a standalone device or may be connected (e.g., networked) to other machines. In a networked deployment, the machine 1100 may operate in the capacity of a server machine, a client machine, or both in server-client network environments. In an example, the machine 1100 may act as a peer machine in peer-to-peer (P2P) (or other distributed) network environment. The machine 1100 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), among other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1100 may include a hardware processor 1102 (e.g., a central processing unit (CPU), a graphics processing unit (GPU), a hardware processor core, algorithm specific ASIC, or any combination thereof), a main memory 1104 and a static memory 1106, some or all of which may communicate with each other via an interlink (e.g., bus) 1108. The machine 1100 may further include a display unit 1110 (e.g., a raster display, vector display, holographic display, etc.), an alphanumeric input device 1112 (e.g., a keyboard), and a user interface (UI) navigation device 1114 (e.g., a mouse). In an example, the display unit 1110, input device 1112 and UI navigation device 1114 may be a touch screen display. The machine 1100 may additionally include a storage device (e.g., drive unit) 1116, a signal generation device 1118 (e.g., a speaker), a network interface device 1120, and one or more sensors 1121, such as a global positioning system (GPS) sensor, compass, accelerometer, or other sensors. The machine 1100 may include an output controller 1128, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1116 may include a machine readable medium 1122 on which is stored one or more sets of data structures or instructions 1124 (e.g., software) embodying or utilized by any one or more of the techniques or functions described herein. The instructions 1124 may also reside, completely or at least partially, within the main memory 1104, within static memory 1106, or within the hardware processor 1102 during execution thereof by the machine 1100. In an example, one or any combination of the hardware processor 1102, the main memory 1104, the static memory 1106, or the storage device 1116 may constitute machine readable media.

While the machine-readable medium 1122 is illustrated as a single medium, the term "machine readable medium" may include a single medium or multiple media (e.g., a centralized or distributed database, and/or associated caches and servers) configured to store the one or more instructions 1124.

The term "machine readable medium" may include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 1124 may further be transmitted or received over a communication network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1120 may include one or more physical jacks (e.g., Ethernet, coaxial, or phone jacks) or one or more antennas to connect to the communication network 1126. In an example, the network interface device 1120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software.

Various examples are illustrated in the figures above. One or more features from one or more of these examples may be combined to form other examples.

The method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for providing electrostimulation to a patient, comprising:

an implantable stimulator configured to provide electrostimulation to a neural target of the patient via a lead comprising a plurality of electrodes;

a programming device configured to:

under a first patient state, evaluate a clinical response indicator using clinical effect data collected from the patient in response to electrostimulation delivered in accordance with first stimulation settings defined in a search space of electrode configurations and parameter values for the lead with respect to the neural target; and identify a subspace of the search space based at least in part on the clinical response indicator associated with the first stimulation settings, the identified subspace comprising stimulation positions and a stimulation parameter value zone defined between first and second characteristic parameter values for each of the stimulation positions, the first and second characteristic parameter values each corresponding to respective clinical response indicators satisfying respective conditions; and a therapy titration device configured to:

under a second patient state different from the first patient state, evaluate the clinical response indicator using clinical effect data collected from the patient in response to electrostimulation delivered in accordance with candidate stimulation settings defined in the identified subspace;

select a stimulation setting from the candidate stimulation settings based at least in part on the clinical response indicator associated with the candidate stimulation settings, the selected stimulation setting including a stimulation parameter value falling within the stimulation parameter value zone; and generate a control signal to the implantable stimulator to deliver electrostimulation in accordance with the selected stimulation setting.

2. The system of claim 1, wherein the stimulation parameter value zone is defined between the first and second characteristic parameter values each modified by respective margins.

3. The system of claim 1, wherein the stimulation parameter includes a stimulation amplitude, the stimulation parameter value zone includes a stimulation amplitude zone defined between (i) a first characteristic stimulation amplitude corresponding to a clinical response indicator indicating an improvement in patient symptom from a baseline and (ii) a second stimulation amplitude corresponding to a clinical response indicator indicating a side effect or a loss of improvement of patient symptom from the baseline.

4. The system of claim 1, wherein the stimulation positions include a plurality of vertical electrode locations on the lead, and wherein the stimulation parameter value zone comprises stimulation parameter value ranges for the plurality of vertical electrode locations.

5. The system of claim 1, wherein the stimulation positions include a plurality of directional electrode locations at a common vertical location on the lead, and wherein the stimulation parameter value zone comprises stimulation parameter value ranges for the plurality of directional electrode locations.

6. The system of claim 1, wherein the therapy titration device is configured to be communicatively coupled to a cloud-computing system, and to use cloud-based services from the cloud-computing system to evaluate the clinical response indicator or to select the stimulation setting.

7. The system of claim 6, wherein the cloud-based services include automatically downloading one or more the candidate stimulation settings into the therapy titration device and initiating the electrostimulation in accordance with the candidate stimulation settings.

8. The system of claim 6, wherein the cloud-based services include collecting and storing in a cloud storage the clinical effect data in response to the electrostimulation delivered in accordance with candidate stimulation settings.

9. The system of claim 8, wherein the therapy titration device is configured to collect the clinical effect data including at least one of:

a user feedback on clinical effects of the electrostimulation via a user interface; or sensor signals sensed by one or more sensors in response to the electrostimulation delivered in accordance with candidate stimulation settings.

10. The system of claim 1, wherein:

the implantable stimulator is configured to provide deep brain electrostimulation (DBS) to a brain target via one or more leads each configured to be positioned in a left or right hemisphere of the brain;

the programming device is configured to identify a first subspace comprising stimulation positions and the stimulation parameter values or value ranges for DBS of the left hemisphere of the brain, and to separately identify a second subspace comprising stimulation positions and the stimulation parameter values or value ranges for DBS of the right hemisphere of the brain; and the therapy titration device is configured to select a first stimulation setting from the first subspace for the DBS of the left hemisphere, and a second stimulation setting from the second subspace for the DBS of the right hemisphere.

11. A method of providing electrostimulation using a medical-device system, the method comprising:

under a first patient state, delivering electrostimulation to a neural target using an implantable stimulator coupled to a lead comprising a plurality of electrodes, the electrostimulation delivered in accordance with first stimulation settings defined in a search space of electrode configurations and parameter values;

collecting clinical effect data from the patient in response to the electrostimulation and evaluating a clinical response indicator using the collected clinical effect data;

identifying a subspace of the search space based at least in part on the clinical response indicator associated with the first stimulation settings, the identified subspace comprising stimulation positions and a stimulation parameter value zone defined between first and second characteristic parameter values for each of the stimulation positions, the first and second characteristic parameter values each corresponding to respective clinical response indicators satisfying respective conditions;

under a second patient state different from the first patient state, delivering electrostimulation to the neural target using the implantable stimulator, the electrostimulation delivered in accordance with candidate stimulation settings defined in the identified subspace;

collecting the clinical effect data from the patient in response to the electrostimulation and evaluating a clinical response indicator using the collected clinical effect data;

selecting a stimulation setting from the candidate stimulation settings based at least in part on the clinical response indicator associated with the candidate stimulation settings, the selected stimulation setting including a stimulation parameter value falling within the stimulation parameter value zone; and generating a control signal to the implantable stimulator to deliver electrostimulation in accordance with the selected stimulation setting.

12. The method of claim 11, comprising:

without delivering electrostimulation to the patient, estimating clinical effect data for second stimulation settings defined in the search space different than the first stimulation settings based at least on the collected clinical effect data corresponding to the first stimulation settings;

evaluating the clinical response indicator further using the estimated clinical effect data; and identifying the subspace further based on the clinical response indicator associated with the second stimulation settings.

13. The method of claim 11, wherein the stimulation parameter value zone is defined between the first and second characteristic parameter values each modified by respective margins.

14. The method of claim 11, wherein the stimulation parameter includes a stimulation amplitude, the stimulation parameter value zone includes a stimulation amplitude zone defined between (i) a first characteristic stimulation amplitude corresponding to a clinical response indicator indicating an improvement in patient symptom from a baseline and (ii) a second stimulation amplitude corresponding to a clinical response indicator indicating a side effect or a loss of improvement of patient symptom from the baseline.

15. The method of claim 11, comprising:

receiving cloud-based services from a cloud-computing system; and using the received cloud-based services to initiate the electrostimulation in accordance with the candidate stimulation settings, to evaluate the clinical response indicator, or to select the stimulation setting.

16. The method of claim 15, wherein the cloud-based services include collecting and storing in a cloud storage the clinical effect data in response to the electrostimulation delivered in accordance with candidate stimulation settings, wherein the clinical effect data includes at least one of a user feedback on clinical effects of the electrostimulation via a user interface, or sensor signals sensed by one or more sensors in response to the electrostimulation delivered in accordance with candidate stimulation settings.

17. A system for providing electrostimulation to a patient, comprising:

an implantable stimulator configured to provide electrostimulation to a neural target of the patient via a lead comprising a plurality of electrodes;

a programming device configured to:

under a first patient state, evaluate a clinical response indicator using (i) first clinical effect data collected from the patient in response to electrostimulation delivered in accordance with first stimulation settings defined in a search space of electrode configurations and parameter values for the lead with respect to the neural target, and (ii) second clinical effect data estimated for second stimulation settings defined in the search space different than the first stimulation settings without delivering electrostimulation to the patient, the second clinical effect data estimated based at least on the collected clinical effect data corresponding to the first stimulation settings; and identify a subspace of the search space based at least in part on the clinical response indicator associated with the first and the second stimulation settings; and a therapy titration device configured to:

under a second patient state different from the first patient state, evaluate the clinical response indicator using clinical effect data collected from the patient in response to electrostimulation delivered in accordance with candidate stimulation settings defined in the identified subspace;

select a stimulation setting from the candidate stimulation settings based at least in part on the clinical response indicator associated with the candidate stimulation settings; and generate a control signal to the implantable stimulator to deliver electrostimulation in accordance with the selected stimulation setting.

18. The system of claim 17, wherein the programming device is further configured to:

determine, under the first patient state, at least one base stimulation setting corresponding to the clinical response indicator associated with the first stimulation settings or the second stimulation settings satisfying a specific condition, the at least one base stimulation setting including an optimal electrode configuration and an optimal stimulation parameter value; and identify the subspace based on the clinical response indicator of the at least one base stimulation setting.

19. The system of claim 17, wherein the therapy titration device is configured to be communicatively coupled to a cloud-computing system, and to use cloud-based services from the cloud-computing system to evaluate the clinical response indicator or to select the stimulation setting.

20. The system of claim 17, wherein:

the implantable stimulator is configured to provide deep brain electrostimulation (DBS) to a brain target via one or more leads each configured to be positioned in a left or right hemisphere of the brain;

the programming device is configured to identify a first subspace comprising stimulation positions and the stimulation parameter values or value ranges for DBS of the left hemisphere of the brain, and to separately identify a second subspace comprising stimulation positions and the stimulation parameter values or value ranges for DBS of the right hemisphere of the brain; and the therapy titration device is configured to select a first stimulation setting from the first subspace for the DBS of the left hemisphere, and a second stimulation setting from the second subspace for the DBS of the right hemisphere.

* * * * *